United States Patent
Olsen et al.

(10) Patent No.: US 12,357,496 B2
(45) Date of Patent: Jul. 15, 2025

(54) SENSOR ASSEMBLY FOR OSTOMY APPLIANCE

(71) Applicant: Coloplast A/S, Humlebaek (DK)

(72) Inventors: Frank Edberg Olsen, Vanloese (DK); Lars Molzen, Alleroed (DK); Jais Ask Hansen, Jaegerspris (DK); Jose Manuel Roman-Marin, Copenhagen N (DK); Jesper Kenneth Olsen, Birkeroed (DK); Jonas Emborg, Frederikssund (DK)

(73) Assignee: Coloplast A/S, Humlebaek (DK)

( * ) Notice: Subject to any disclaimer, the term of this patent is extended or adjusted under 35 U.S.C. 154(b) by 461 days.

(21) Appl. No.: 17/918,626

(22) PCT Filed: Apr. 14, 2021

(86) PCT No.: PCT/DK2021/050107
§ 371 (c)(1),
(2) Date: Oct. 13, 2022

(87) PCT Pub. No.: WO2021/209107
PCT Pub. Date: Oct. 21, 2021

(65) Prior Publication Data
US 2023/0172745 A1 Jun. 8, 2023

(30) Foreign Application Priority Data

Apr. 14, 2020 (DK) .......................... PA 2020 70222

(51) Int. Cl.
*A61F 5/44* (2006.01)
*A61F 5/443* (2006.01)
(Continued)

(52) U.S. Cl.
CPC ............ *A61F 5/4404* (2013.01); *A61F 5/443* (2013.01); *A61F 5/445* (2013.01); *G01V 3/02* (2013.01); *H01B 13/0036* (2013.01)

(58) Field of Classification Search
CPC ........ A61F 5/4404; A61F 5/443; A61F 5/445; G01V 3/02; H01B 13/0036
See application file for complete search history.

(56) References Cited

U.S. PATENT DOCUMENTS 10,500,084 B2 * 12/2019 Hansen ................... A61F 5/445
10,799,385 B2 * 10/2020 Hansen ................... G01M 3/40
(Continued)

FOREIGN PATENT DOCUMENTS

| WO | 2019120424 A1 | 6/2019 | |
| WO | WO-2019120453 A1 * | 6/2019 | .......... A61B 5/4851 |
| WO | 2020076609 A1 | 4/2020 | |

*Primary Examiner* — Guy K Townsend
(74) *Attorney, Agent, or Firm* — Coloplast Corp., Coloplast A/S; Nick Baumann

(57) ABSTRACT

Sensor assembly, for an ostomy appliance, comprising a support layer and a planar electrode assembly arranged on a surface of the support layer. The electrode assembly comprises at least a first electrode. The first electrode comprises a first main branch extending along a first main path and a first plurality of subbranches connected to the first main branch. Each of the subbranches are connected to the first main branch at respective connection points and extend in a direction at an angle relative to a tangent to the first main path at the respective connection point. Thereby is provided that a rupture of one of the subbranches does not compromise the functionality of the first electrode as such.

15 Claims, 11 Drawing Sheets

(51) Int. Cl.
    *A61F 5/445*     (2006.01)
    *G01V 3/02*     (2006.01)
    *H01B 13/00*     (2006.01)

(56) References Cited

U.S. PATENT DOCUMENTS

| | | | |
|---|---|---|---|
| 11,547,596 B2* | 1/2023 | Hansen | A61F 5/44 |
| 2019/0133810 A1 | 5/2019 | Seres et al. | |
| 2019/0192333 A1* | 6/2019 | Hansen | A61F 5/445 |
| 2019/0192334 A1* | 6/2019 | Hansen | A61F 5/445 |
| 2020/0000624 A1 | 1/2020 | Gibbons et al. | |
| 2020/0246175 A1* | 8/2020 | Hansen | G01M 3/16 |
| 2020/0246176 A1* | 8/2020 | Hansen | A61F 5/445 |
| 2020/0330258 A1* | 10/2020 | Hansen | A61F 13/511 |
| 2020/0337880 A1* | 10/2020 | Hansen | A61F 5/443 |
| 2020/0337881 A1* | 10/2020 | Hansen | A61F 5/4404 |
| 2020/0375499 A1* | 12/2020 | Hansen | A61B 5/4216 |
| 2020/0375784 A1* | 12/2020 | Hansen | A61F 5/443 |
| 2020/0383820 A1* | 12/2020 | Hansen | G16H 40/40 |
| 2020/0383821 A1* | 12/2020 | Hansen | A61F 5/443 |
| 2020/0390587 A1* | 12/2020 | Svanegaard | G16H 40/40 |
| 2020/0390589 A1* | 12/2020 | Hansen | A61F 5/443 |
| 2020/0395120 A1* | 12/2020 | Svanegaard | G06F 3/0482 |
| 2020/0405228 A1* | 12/2020 | Svanegaard | A61F 5/4404 |
| 2021/0000634 A1* | 1/2021 | Svanegaard | A61B 5/0004 |
| 2022/0265457 A1* | 8/2022 | Emborg | A61F 5/4404 |
| 2023/0172745 A1* | 6/2023 | Olsen | A61F 5/443 |
| | | | 604/344 |

* cited by examiner

SENSOR ASSEMBLY FOR OSTOMY APPLIANCE

The present disclosure relates to a sensor assembly for an ostomy appliance, the sensor assembly having an electrode assembly. Further, the present disclosure relates to a method of manufacturing such a sensor assembly and a base plate comprising such a sensor assembly.

BRIEF DESCRIPTION OF THE DRAWINGS

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
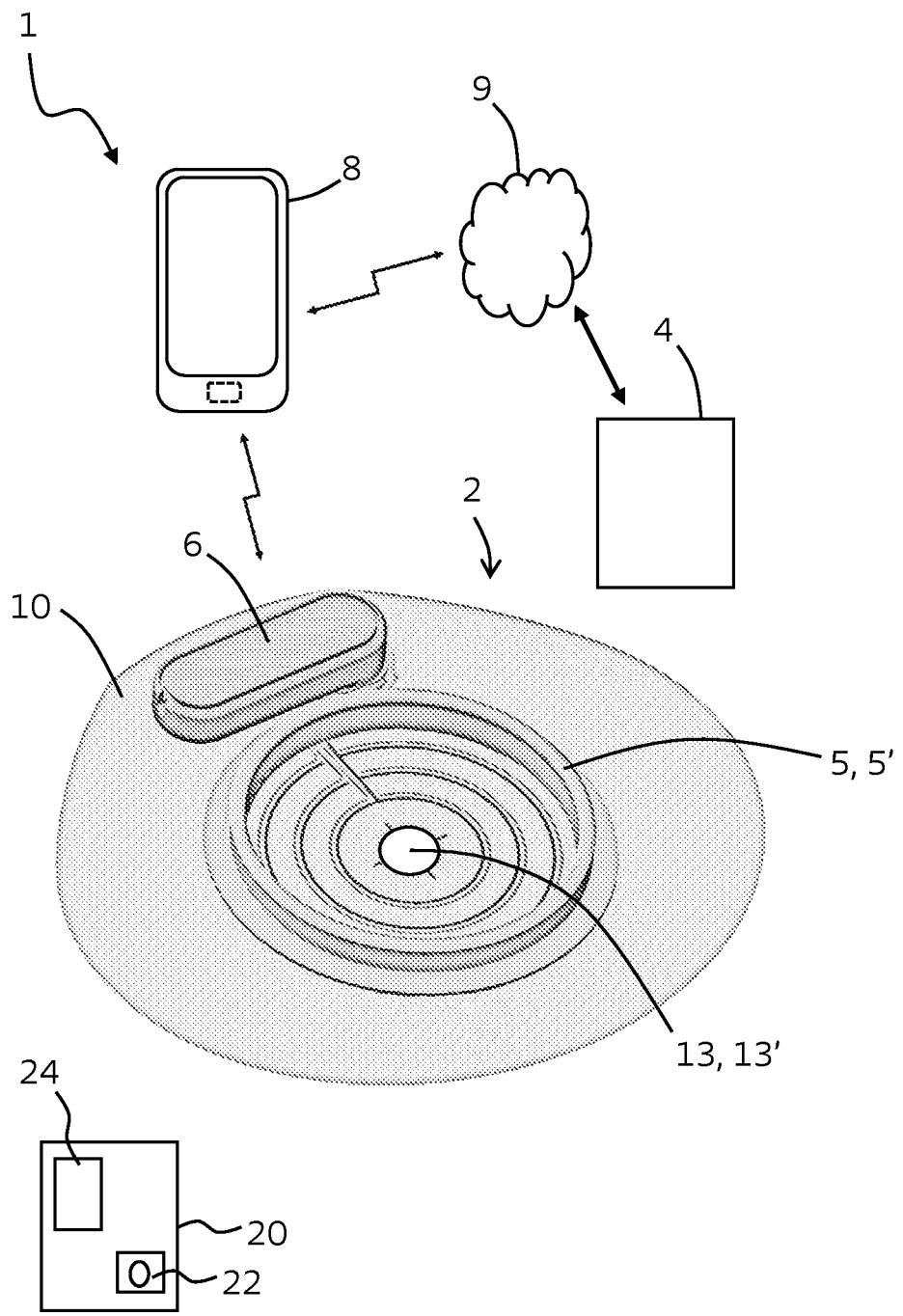
FIG. 1 illustrates an exemplary ostomy system.

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

Throughout this disclosure, the words "stoma" and "ostomy" are used to denote a surgically created opening bypassing the intestines or urinary tract system of a person. The words are used interchangeably, and no differentiated meaning is intended. The same applies for any words or phrases derived from these, e.g. "stomal", "ostomies" etc. Also, the solid and liquid wastes emanating from the stoma may be referred to as both stomal "output," "waste(s)," "liquids," and "fluids" interchangeably. A subject having undergone ostomy surgery may be referred to as "ostomist" or "ostomate"— moreover, also as "patient" or "user". However, in some cases "user" may also relate or refer to a health care professional (HCP), such as a surgeon or an ostomy care nurse or others. In those cases, it will either be explicitly stated, or be implicit from the context that the "user" is not the "patient" him— or herself.

In the following, whenever referring to proximal side or surface of a layer, an element, a device or part of a device, the referral is to the skin-facing side or surface, when a user wears the ostomy appliance. Likewise, whenever referring to the distal side or surface of a layer, an element, a device or part of a device, the referral is to the side or surface facing away from the skin, when a user wears the ostomy appliance. In other words, the proximal side or surface is the side or surface closest to the user, when the appliance is fitted on a user and the distal side is the opposite side or surface—the side or surface furthest away from the user in use.

The axial direction is defined as the direction of the stoma, when a user wears the appliance. Thus, the axial direction is generally perpendicular to the skin or abdominal surface of the user.

A radial direction is defined as perpendicular to the axial direction. In some sentences, the words "inner" and "outer" may be used. These qualifiers should generally be perceived with respect to the radial direction, such that a reference to an "outer" element means that the element is farther away from a centre portion of the ostomy appliance than an element referenced as "inner". In addition, "innermost" should be interpreted as the portion of a component forming a centre of the component and/or being adjacent to the centre of the component. In analogy, "outermost" should be interpreted as a portion of a component forming an outer edge or outer contour of a component and/or being adjacent to that outer edge or outer contour.

The use of the word "substantially" as a qualifier to certain features or effects in this disclosure is intended to simply mean that any deviations are within tolerances that would normally be expected by the skilled person in the relevant field.

The present disclosure relates to an ostomy system and devices thereof, such as an ostomy appliance, a base plate for an ostomy appliance, a sensor patch for application to a base plate, one or more monitor devices, and optionally one or more accessory devices. Further, methods related to the ostomy system and devices thereof are disclosed. An accessory device (also referred to as an external device) can be a mobile phone or other handheld device. In embodiments, an accessory device is a personal electronic device, e.g. a wearable, such as a watch or other wrist-worn electronic device. An accessory device can be a docking station. In embodiments, the docking station is configured to electrically and/or mechanically couple the monitor device to the docking station. In embodiments, the docking station is configured for charging a battery of the monitor device and/or configured for transferring data between the monitor device and the docking station. The ostomy system can comprise a server device. In embodiments, the server device is operated and/or controlled by the ostomy appliance manufacturer and/or a service centre.

The present disclosure provides an ostomy system and devices thereof, such as an ostomy appliance, a base plate for an ostomy appliance, a sensor patch for application to a base plate, a sensor assembly for an ostomy appliance, e.g. a base plate or a sensor patch of an ostomy appliance, a monitor device, and optionally one or more accessory devices which either alone or together facilitate reliable determination of the nature, severity, and rapidness of leakage propagation in the interface between a skin surface and the base plate and/or moisture propagation in the adhesive material provided for attaching the base plate and/or sensor patch to the skin surface of a user. Depending on the nature of the pattern of leakage and/or moisture propagation in the adhesive, the ostomy system and devices thereof enable providing information to the user about the type of failure, and in turn enable providing an indication to the user of the severity and thus the remaining time frame for replacing the ostomy appliance without experiencing severe leakage and/or skin damage.

Determination of moisture pattern types or (angular) leakage patterns is useful in helping to reduce the risk of a user experiencing leakage from an ostomy appliance. Further, determination of moisture pattern types and classification of operating states and/or leakage patterns of the ostomy appliance is further useful in helping reduce the risk of skin damage to a user.

In a first aspect of the invention, a sensor assembly for an ostomy appliance is provided. The sensor assembly comprises a support layer and a planar electrode assembly arranged on a surface of the support layer. The electrode assembly comprises at least a first electrode. The first electrode comprises a first main branch extending along a first main path and a first plurality of subbranches connected to the first main branch. The first plurality of subbranches includes a first primary subbranch and a first secondary subbranch. The first primary subbranch is connected to the first main branch at a first primary connection point and extending in a first primary direction at a first primary angle relative to a tangent to the first main path at the first primary connection point. The first secondary subbranch is connected to the first main branch at a first secondary connection point and extending in a first secondary direction at a first secondary angle relative to a tangent to the first main path at the first secondary connection point By providing a plurality of subbranches on a main branch of a given first electrode, a rupture of one of the plurality of subbranches does not compromise the functionality of the remaining subbranches and the main branch as such, where by functionality is meant the ability to conduct a signal, e.g. a current. For example, where the sensor assembly is incorporated in a base plate or a sensor patch for attachment to a base plate as discussed in exemplary embodiments throughout the present disclosure, a user may stretch the base plate or sensor patch, and thus the sensor assembly, to provide an adequate fit according to his/her needs or anatomy. During such stretching/handling of the base plate or sensor patch, one or more electrodes of the electrode assembly of the sensor assembly may rupture due to inherent material properties (e.g., a low Young's modulus) of the electrodes limiting their stretchability. However, by providing an electrode having a plurality of subbranches connected to a main branch, the risk of compromising the functionality of the entire electrode through rupturing of the main branch is reduced: rather, it may be that one or more of the subbranches are ruptured (becomes electrically disconnected from the main branch), whereby the functionality of the affected one or more subbranches is compromised, but not the functionality of the entire electrode.

In embodiments, the first main branch is reinforced with respect to the subbranches, e.g. by means of material properties (e.g., using a different conductive material for the first main branch than for the subbranches), sizing (e.g., providing a thicker and/or wider first main branch than the subbranches), or additional features, such as stretch-inhibiting features (e.g., by bonding a stretch-inhibiting layer to the support layer in the vicinity of the first main branch). Thereby, stretching or irregular handling of the base plate or sensor patch comprising the sensor assembly is more likely to cause rupture of the subbranches (e.g., rupturing the electrical connection between the subbranch and the main branch) than of the main branch, thereby ensuring the functionality of the electrode remains largely unaffected: only the sensing abilities of the ruptured subbranch is lost—not the sensing abilities of the remaining subbranches and/or the sensing abilities of the main branch as such.

Finally, subbranches extending away from the first main branch provide for covering a larger area, such that a larger area may be covered by a single electrode, such as to increase the area where electrical properties of a medium in contact with the electrode may be measured. Measurements of electrical properties of a medium in contact with the electrode/sensor assembly is described in further detail below.

In embodiments, the ostomy appliance comprises a base plate and an ostomy pouch (also referred to as an ostomy bag). The ostomy appliance can be a colostomy appliance, an ileostomy appliance, or a urostomy appliance. In embodiments, the ostomy appliance is a two-part ostomy appliance, i.e. the base plate and the ostomy pouch are releasably coupled e.g. with a mechanical and/or an adhesive coupling, e.g. to allow that a plurality of ostomy pouches can be utilized (exchanged) with one base plate. Further, a two-part ostomy appliance can facilitate correct application of the base plate to skin, e.g. to an improved user sight of the stomal region. In embodiments, the ostomy appliance is a one-part ostomy appliance, i.e. the base plate and the ostomy pouch are fixedly attached to each other. The base plate is configured for coupling to a user's stoma and/or skin surrounding the stoma, such as a peristomal skin area.

In embodiments, the ostomy appliance includes a base plate, such as a monolithic, one-piece base plate, e.g. integrated with a sensor assembly, or a separate sensor assembly part, such as a sensor assembly part to be subsequently applied to a base plate. In embodiments, the sensor assembly comprises at least the sensor assembly according to the present disclosure. In embodiments, the sensor assembly part is a sensor patch for application to the base plate, such as the proximal surface of the base plate. Thereby, an arbitrary base plate, such as a conventional base plate, can achieve the features as described herein. Features as described with respect to sensing/monitoring capabilities of the base plate herein can be provided by a sensor assembly of a sensor patch to be applied to a base plate, e.g. by the user, and vice versa. In embodiments, the sensor patch is adapted to adhere to a base plate.

In embodiments, a method of attaching a base plate having sensing capabilities, e.g. through the provision of a sensor patch, to a user's stoma and/or skin surrounding the stoma, such as the peristomal skin area, comprises attaching the sensor patch to a base plate and attaching the base plate, i.e. together with the attached sensor patch, to the user's stoma and/or skin surrounding the stoma, such as the peristomal skin area. Alternatively, the method of attaching the base plate to the user's stoma and/or skin surrounding the stoma comprises attaching the sensor patch to the user's stoma and/or skin surrounding the stoma and attaching the base plate to the user's stoma and/or skin surrounding the stoma above the attached sensor patch, i.e. on a distal surface of the sensor patch.

In embodiments, the base plate and/or the sensor patch comprises a first adhesive layer with a proximal side configured for attachment of the base plate and/or the sensor patch to the skin surface of a user. In embodiments, the first adhesive layer has a stomal opening, such as a first adhesive stomal opening, with a centre point.

In embodiments, the base plate and/or sensor patch comprises at least one electrode, such as a plurality of electrodes including a first electrode, a second electrode, and a third electrode provided in an electrode assembly of a sensor assembly, such as the sensor assembly according to the present disclosure. In embodiments, the plurality of electrodes is configured to detect presence of liquid, such as output, on the proximal side of the first adhesive layer and/or moisture content in the first adhesive layer. In embodiments, the electrode assembly of the sensor assembly is configured to detect presence of liquid, such as output, on the proximal side of the first adhesive layer and/or moisture content in the first adhesive layer in a primary sensing zone and a secondary sensing zone. In embodiments, the primary sensing zone is arranged in a primary angle space from the centre point of the first adhesive layer, and/or the secondary sensing zone is arranged in a secondary angle space, separate from the primary angle space, from the centre point of the first adhesive layer. Alternatively, or additionally, the primary sensing zone can be arranged in a primary radial space from the centre point of the first adhesive layer and the secondary sensing zone can be arranged in a secondary radial space from the centre point of the first adhesive layer. In embodiments, the electrode assembly of the sensor assembly is configured to detect presence of liquid, such as output, on the proximal side of the first adhesive layer and/or moisture content in the first adhesive layer in three or more sensing zones.

In embodiments, the monitor device of the ostomy system comprises a housing, a processor, a memory, a first interface (also referred to as an appliance interface) connected to the processor and the memory, and a second interface connected to the processor. The first interface is configured for obtaining ostomy data from the sensor assembly, e.g. from the base plate and/or the sensor patch comprising the sensor assembly and coupled to the first interface. The ostomy data comprises primary ostomy data from a primary electrode set of the sensor assembly of the base plate and/or the sensor patch, and secondary ostomy data from a secondary electrode set of the sensor assembly of the base plate and/or the sensor patch. In embodiments, the processor is configured to: obtain primary parameter data based on the primary ostomy data; obtain secondary parameter data based on the secondary ostomy data; and detect presence of liquid on the proximal side of the first adhesive layer and/or moisture in the first adhesive layer in a primary sensing zone based on the primary parameter data. In embodiments, the primary sensing zone is arranged in a primary angle space from the centre point of the first adhesive layer and/or arranged in a primary radial space from the centre point of the first adhesive layer. Further, in embodiments, the processor is configured to detect presence of liquid on the proximal side of the first adhesive layer and/or moisture in the first adhesive layer in a secondary sensing zone based on the secondary parameter data. In embodiments, the secondary sensing zone is arranged in a secondary angle space from the centre point of the first adhesive layer and/or arranged in a secondary radial space from the centre point of the first adhesive layer. In embodiments, in accordance with a detection of presence of liquid and/or moisture in the primary sensing zone, the processor is configured to transmit a primary monitor signal comprising monitor data indicative of presence of liquid and/or moisture in the primary sensing zone via the second interface; and in accordance with a detection of presence of liquid and/or moisture in the secondary sensing zone, transmit a secondary monitor signal comprising monitor data indicative of presence of liquid and/or moisture in the secondary sensing zone via the second interface.

The base plate and/or the sensor patch comprises a first adhesive layer. During use, the first adhesive layer adheres to the user's skin (peristomal area) and/or to additional seals, such as sealing paste, sealing tape and/or sealing ring. Thus, in embodiments, the first adhesive layer is configured for attachment of the base plate and/or the sensor patch to the skin surface of a user. In embodiments, the first adhesive layer has a stomal opening, such as a first adhesive stomal opening, with a centre point or is at least prepared for forming a stomal opening with a centre point. A base plate and/or a sensor patch comprising a sensor assembly according to the present disclosure enables detection of presence of liquid or output on the proximal side of the first adhesive layer (in the interface between a skin surface of the user, such as the peristomal skin area, and the proximal surface of the first adhesive layer) and/or detection of moisture content in the first adhesive layer.

In embodiments, the first adhesive layer is made of a first composition. In embodiments, the first composition comprises one or more polyisobutenes and/or styrene-isoprene-styrene. In embodiments, the first composition comprises one or more hydrocolloids. In embodiments, the first composition comprises one or more water soluble or water swellable hydrocolloids. In embodiments, the first composition is a pressure sensitive adhesive composition suitable for medical purposes comprising a rubbery elastomeric base and one or more water soluble or water swellable hydrocolloids. In embodiments, the first composition comprises one or more polybutenes, one or more styrene copolymers, one or more hydrocolloids, or any combination thereof. The combination of the adhesive properties of the polybutenes and the absorbing properties of the hydrocolloids renders the first composition suitable for use in ostomy appliances. For example, the styrene copolymer can be a styrene-butadiene-styrene block copolymer or a styrene-isoprene-styrene block copolymer. Preferably, one or more styrene-isoprene-styrene (SIS) block type copolymers are employed. The amount of styrene block-copolymer can be from 5% to 20% of the total adhesive composition. The butene component is suitably a conjugated butadiene polymer selected from polybutadiene, polyisoprene. The polybutenes are preferably present in an amount of from 35-50% of the total adhesive composition. Preferably, the polybutene is polyisobutylene (PIB). Suitable hydrocolloids for incorporation in the first composition are selected from naturally occurring hydrocolloids, semi-synthetic hydrocolloids, and synthetic hydrocolloids. The first composition can comprise 20-60% hydrocolloids. A preferred hydrocolloid is carboxymethyl cellulose (CMC). Optionally, the first composition can contain other components, such as fillers, tackifiers, plasticizers, and/or other additives.

The first adhesive layer can have a substantially uniform thickness. The first adhesive layer can have a thickness in the range from 0.1 mm to 1.5 mm, e.g. in the range from 0.2 mm to 1.2 mm, such as 0.8 mm or 1.0 mm. The first adhesive layer can have a primary thickness in a primary part of the first adhesive layer, e.g. in a primary region within a primary radial distance or in a primary radial distance range from the centre point of the stomal opening. The primary thickness can be in the range from 0.2 mm to 1.5 mm, such as about 1.0 mm. The primary radial distance can be in the range from 20 mm to 50 mm, such as in the range from 25 mm to 35 mm, e.g. 30 mm. The first adhesive layer can have a secondary thickness in a secondary part of the first adhesive layer, e.g. in a secondary region outside a secondary radial distance or in a secondary radial distance range from the centre point of the stomal opening. The secondary thickness can be in the range from 0.2 mm to 1.0 mm, such as about 0.5 mm. The secondary radial distance can be in the range from 20 mm to 50 mm, such as in the range from 25 mm to 35 mm, e.g. 30 mm.

In embodiments, the base plate and/or the sensor patch comprises a second layer. In embodiments, the second layer is an adhesive layer. In embodiments, the second layer has a second radial extension that is larger than a first radial extension of the first adhesive layer at least in a first angular range of the base plate and/or the sensor patch. Accordingly, a part of a proximal surface of the second layer can be configured for attachment to the skin surface of a user. The part of a proximal surface of the second layer configured for attachment to the skin surface of a user is also denoted the skin attachment surface of the second adhesive layer. The second layer can have a stomal opening, such as a second layer stomal opening and/or a second adhesive stomal opening, with a centre point.

In embodiments, the second adhesive layer is made of a second composition. In embodiments, the second composition comprises one or more polyisobutenes and/or styrene-isoprene-styrene. In embodiments, the second composition comprises one or more hydrocolloids. In embodiments, the second composition comprises one or more water soluble or water swellable hydrocolloids. In embodiments, the second composition is a pressure sensitive adhesive composition suitable for medical purposes comprising a rubbery elastomeric base and one or more water soluble or water swellable hydrocolloids. In embodiments, the second composition comprises one or more polybutenes, one or more styrene copolymers, one or more hydrocolloids, or any combination thereof. The combination of the adhesive properties of the polybutenes and the absorbing properties of the hydrocolloids renders the second composition suitable for use in ostomy appliances. For example, the styrene copolymer can be a styrene-butadiene-styrene block copolymer or a styrene-isoprene-styrene block copolymer. Preferably, one or more styrene-isoprene-styrene (SIS) block type copolymers are employed. The amount of styrene block-copolymer can be from 5% to 20% of the total adhesive composition. The butene component is suitably a conjugated butadiene polymer selected from polybutadiene, polyisoprene. The polybutenes are preferably present in an amount of from 35-50% of the total adhesive composition. Preferably, the polybutene is polyisobutylene (PIB). Suitable hydrocolloids for incorporation in the second composition are selected from naturally occurring hydrocolloids, semisynthetic hydrocolloids, and synthetic hydrocolloids. The second composition can comprise 20-60% hydrocolloids. A preferred hydrocolloid is carboxymethyl cellulose (CMC). Optionally, the second composition can contain other components, such as fillers, tackifiers, plasticizers, and/or other additives.

Different ratio of contents can change properties of the first and/or second adhesive layers. In embodiments, the second adhesive layer and the first adhesive layer have different properties. In embodiments, the second adhesive layer (second composition) and the first adhesive layer (first composition) have different ratios of polyisobutenes, styrene-isoprene-styrene, and/or hydrocolloids. For example, the second adhesive layer can provide a stronger attachment to the skin compared to attachment to the skin provided by the first adhesive layer. Alternatively, or additionally, the second adhesive layer can be thinner than the first adhesive layer. Alternatively, or additionally, the second adhesive layer can be less water and/or sweat absorbing than the first adhesive layer. Alternatively, or additionally, the second adhesive layer can be less mouldable than the first adhesive layer. In embodiments, the second adhesive layer provides a second barrier against leakage.

The second layer can have a substantially uniform thickness. The second layer can have a thickness in the range from 0.1 mm to 1.5 mm, e.g. in the range from 0.2 mm to 1.0 mm, such as 0.5 mm, 0.6 mm, or 0.7 mm.

Providing a base plate having sensing capabilities, e.g. through an incorporated sensor assembly or through a sensor patch comprising a sensor assembly, such as a sensor assembly according to the present disclosure, provides for an optimum or improved use of an ostomy appliance. In particular, it is facilitated that a base plate is not changed too late (leading to adhesive failure, leakage, and/or skin damage), or at least that a user is informed that a leakage will happen, is happening, or has happened. Accordingly, the user or a health care professional is able to monitor and plan the use of the ostomy appliance.

In embodiments, the base plate and/or the sensor patch comprises one or more electrodes, such as a plurality of electrodes, such as two, three, four, five, six, seven or more electrodes. In embodiments, the electrodes are provided in an electrode assembly. In embodiments, the electrode assembly is provided in a sensor assembly, such as the sensor assembly according to the present disclosure.

In embodiments, the electrodes, e.g. some or all the electrodes, such as the sensor assembly comprising the electrode assembly comprising the electrodes, are arranged on a distal side of the first adhesive layer, such as between the first adhesive layer and the second adhesive layer of the base plate and/or sensor patch. In embodiments, an electrode comprises a connection part for connecting the electrode to other components and/or interface terminals/terminal elements, such as for connecting the electrode to a monitor device. The electrode assembly can comprise a first electrode, such as a first electrode according to the present disclosure, and a second electrode and optionally a third electrode. The electrode assembly can comprise a fourth electrode and/or a fifth electrode. The electrode assembly optionally comprises a sixth electrode. In embodiments, the electrode assembly comprises a ground electrode. The ground electrode can comprise a first electrode part. In embodiments, the first electrode part of the ground electrode forms a ground or reference for the first electrode. In embodiments, the first electrode part forms a closed loop. The ground electrode can comprise a second electrode part. In embodiments, the second electrode part of the ground electrode forms a ground or reference for the second electrode. The ground electrode can comprise a third electrode part. In embodiments, the third electrode part of the ground electrode forms a ground or reference for the third electrode. The ground electrode can comprise a fourth electrode part. In embodiments, the fourth electrode part of the ground electrode forms a ground or reference for the fourth electrode and/or the fifth electrode. In embodiments, the ground electrode is configured as, or forms a, (common) reference electrode for some or all of the other electrodes of the electrode assembly. In embodiments, the ground electrode is the electrical ground electrode relative to additional electrodes when a voltage is applied to the electrodes of the electrode assembly. In embodiments, the voltage is applied by means of the monitor device. In embodiments, applying a voltage allows for determining electrical properties, such as resistance, such as resistance of the adhesive layer and/or liquid in contact with the electrodes of the electrode assembly.

The one or more electrodes of the electrode assembly are electrically conductive and can comprise one or more of metallic (e.g. silver, copper, gold, titanium, aluminum, stainless steel or other), ceramic (e.g. ITO or other), polymeric (e.g. PEDOT, PANI, PPy or other), and carbonaceous (e.g. carbon black, carbon nanotube, carbon fiber, graphene, graphite, or other) materials. In embodiments, the electrodes can be wire electrodes or one-dimensional electrodes resembling a string or wire. In embodiments, the electrodes can have a width and/or thickness being considerably smaller than their length. In embodiments, the width and/or thickness of the electrodes can be up to 50 times smaller than the length of the electrodes. In embodiments, the electrodes can be less than 3 mm wide, and more than 100 mm long. In a preferred embodiment, the electrodes of the electrode assembly are printed on a support layer, whereby the electrode assembly comprises, such as consists of, conductive traces of a conductive ink, e.g. silver ink or carbon ink suitable for printing on a surface. Thus, in embodiments the electrode assembly comprises, such as consists of, a (hardened/cured) conductive ink. In embodiments, conductive ink is created by infusing graphite, silver, or other conductive materials, into ink.

According to the first aspect of the invention, the electrode assembly is arranged on, and thus layered with, a support layer, also denoted a support film. In embodiments, the sensor assembly comprises the electrode assembly and the support layer. One or more electrodes can be formed, e.g. printed, thereby forming a conductive trace of conductive ink, on the proximal side of the support layer. One or more electrodes can be formed, e.g. printed, on the distal side of the support layer. Thus, one or more electrodes can be arranged between the support layer and the first adhesive layer. The electrode assembly, such as the support layer of the electrode assembly, can have a stomal opening, such as an electrode assembly stomal opening and/or a support layer stomal opening, with a centre point.

In embodiments, by a support layer or support film is meant a coherent flexible and/or elastic sheet substantially covering, or is adapted to cover, the entire surface or side of an object, such as the first adhesive layer. The support layer of a sensor assembly for an ostomy appliance may serve at least two purposes; it provides a protection for the first adhesive layer and it provides a substrate for the electrode assembly. Thus, the support layer may be denoted a protective support layer. In particular, the support layer may protect the first adhesive layer from dirt and from external stress and strain, such as caused by handling. Further, the support layer provides a certain rigidity/stiffness to the first adhesive layer, thereby easing handling, e.g. when applying the base plate to the skin surface. The support layer may also be denoted a backing layer in the field. In embodiments, the distal and/or proximal surface of the support layer is non-adhesive. In embodiments, the distal and/or proximal surface of the support layer is adhesive.

In embodiments, the support layer is stretchable, flexible and/or elastic. In a preferred embodiment, the support layer is flexible and elastic. In an embodiment, the support layer is made of a polymeric material. In a preferred embodiment, the support layer is made of polyurethane (PU), e.g. thermoplastic polyurethane (TPU). In alternative embodiments, the support layer material can be made of or comprise one or more of PTFE, PVDF, polyester (e.g., PET), a thermoplastic elastomer (TPE), polyimide, polyimide, Ethylene-vinyl acetate (EVA), polyurea, and/or silicones. Exemplary thermoplastic elastomers (TPEs) of the support layer include styrenic block copolymers (TPS, TPE-s), thermoplastic polyolefin elastomers (TPO, TPE-o), thermoplastic Vulcanizates (TPV, TPE-v), thermoplastic polyurethanes (TPU), thermoplastic copolyester (TPC, TPE-E), and thermoplastic polyamides (TPA, TPE-A). In embodiments, the support layer has a thickness of less than 0.1 mm, such as less than 50 µm.

In embodiments, two electrodes of the electrode assembly form a sensor. In embodiments, the first electrode and a second electrode form a primary sensor or primary electrode pair for detecting (e.g. once a voltage is applied) presence of liquid on the proximal side of the first adhesive layer, potentially in a primary sensing zone, or for detecting presence and/or level of moisture in the first adhesive layer, potentially in the primary sensing zone. In embodiments, a second electrode and a third electrode form a secondary sensor or secondary electrode pair for detecting presence of liquid on the proximal side of the first adhesive layer, potentially in a secondary sensing zone being separate from the primary sensing zone, or for detecting presence and/or level of moisture in the first adhesive layer, potentially in the secondary sensing zone. In embodiments, the first electrode and a third electrode form a tertiary sensor or tertiary electrode pair for detecting presence of liquid on the proximal side of the first adhesive layer, potentially in a tertiary sensing zone being separate from the primary and secondary sensing zones, or for detecting presence and/or level of moisture in the first adhesive layer, potentially in the tertiary sensing zone.

In embodiments, the sensor assembly, the base plate, and/or the sensor patch comprises a monitor interface (also referred to as an assembly interface). In embodiments, the monitor interface is configured for electrically and/or mechanically connecting the ostomy appliance (base plate and/or sensor patch), in particular an electrode assembly of a sensor assembly thereof, to the monitor device. In embodiments, the monitor interface is configured for wirelessly connecting the ostomy appliance (base plate and/or sensor patch) to the monitor device. Thus, the monitor interface of the sensor assembly, base plate, and/or the sensor patch can be configured to electrically and/or mechanically couple the electrode assembly, and thus the sensors formed therefrom, and the monitor device.

In embodiments, the monitor interface of the sensor assembly, base plate, and/or the sensor patch comprises, e.g. as part of a first connector of the monitor interface, a coupling part for forming a mechanical connection, such as a releasable coupling between the monitor device and sensor assembly, base plate, and/or the sensor patch. In embodiments, the coupling part is configured to engage with a coupling part of the monitor device for releasably coupling the monitor device to the sensor assembly, base plate, and/or the sensor patch.

According to the first aspect of the invention, the sensor assembly comprises a support layer and a planar electrode assembly. The electrode assembly comprises at least a first electrode. The first electrode comprises a first main branch extending along a first main path and a first plurality of subbranches connected to the first main branch. Each of the subbranches are connected to the first main branch at respective connection points and extend in a direction at an angle relative to a tangent to the first main path at the respective connection point.

The sensor assembly may be the sensor assembly as previously discussed, and as such, the sensor assembly according to the first aspect of the invention may be configured for being layered with, or used in conjunction with, a base plate or a sensor patch for attachment to a base plate. The support layer may have the properties, and may be made from the materials, as discussed above.

The electrode assembly is planar. By planar is meant that the (e.g. entire) electrode assembly, such as the electrodes of the electrode assembly, extends in a certain geometric two-dimensional plane. Thus, by planar is meant that electrode assembly is substantially flat, such that the electrode assembly can be provided, e.g. printed, on a surface of the support layer and subsequently be layered with a base plate or a sensor patch for attachment to a base plate. In embodiments, the electrodes are printed on a surface of the support layer. Thus, in an embodiment, the at least first electrode of the electrode assembly is a conductive trace, the conductive trace being provided/printed on a surface of the support layer, whereby the electrode assembly can be considered planar since the (printed) electrode assembly conforms to the (planar/flat) surface of the support layer. In embodiments, the entirety of the first electrode is a conductive trace of conductive ink formed from a printing process. In embodiments, the electrode assembly consists entirely of conductive traces forming at least the first electrode. Thus, in embodiments, the entirety of the one or more electrodes, such as the first electrode, a second electrode, and a third electrode, of the electrode assembly are conductive traces.

In embodiments, the first electrode is an electrode according to the previously disclosed electrodes. In the following, the structural features of the first electrode are considered. In embodiments, the electrode assembly comprises further electrodes, such as a second electrode, a third electrode, etc. In embodiments, the further electrodes comprise similar structural features as those disclosed in relation to the first electrode. In embodiments, the further electrodes are structurally different from the first electrode. In embodiments, some of the further electrodes comprise similar structural features as those disclosed in relation to the first electrodes, whereas some, e.g. the rest, of the further electrodes are different from the first electrode.

According to the first aspect of the invention, the first electrode comprises a first main branch and a first plurality of subbranches (electrically) connected to the first main branch. The first main branch extends along a first main path. In a preferred embodiment, the first main branch is a continuous/unbroken main branch of the first electrode. In embodiments, the first main path is a first main direction of the first electrode. Thus, the first main path defines the overall shape, direction, and/or extent of the first electrode. A plurality of subbranches are (electrically) connected to the first main branch along the extent of said first main branch. For example, where the first electrode is printed, the first main branch and the plurality of subbranches are printed in a continuous/single printing process, such that the plurality of subbranches is integral/continuous with the first main branch. In embodiments, the first main branch has a length being at least 50 times longer than a width of the first main branch. In embodiments, the first main branch has a width being less than 5 mm, such as less than 3 mm, such as 2 mm, 1 mm, or 0.5 mm.

The first plurality of subbranches includes a first primary subbranch and a first secondary subbranch. In embodiments, the first plurality of subbranches comprises further subbranches, such as a tertiary subbranch and/or a quaternary subbranch. In embodiments, the first plurality of subbranches comprises at least 10 subbranches, such as at least 20 subbranches. In embodiments, the first plurality of subbranches comprises between 10 and 20 subbranches. In embodiments, the first plurality of subbranches comprises maximally 10 subbranches, or maximally 20 subbranches.

The first primary subbranch is connected to the first main branch at a first primary connection point. Likewise, the first secondary subbranch is connected to the first main branch at a first secondary connection point. By a connection point is meant a point along the first main path of the first main branch where a subbranch is connected to the first main branch. In embodiments, connection points, and as such subbranches, are distributed evenly along the extent of the first main branch. In embodiments, a connection point resembles a "T" intersection, where the stem of the letter "T" forms part of the subbranch, and the bar of the letter "T" forms part of the first main branch, such that the connection point is the intersection between the stem (subbranch) and the bar (main branch). The first primary subbranch extends in a first primary direction at a first primary angle relative to a tangent to the first main path at the first primary connection point. Using the analogy to the "T" intersection, the stem (thus, the first primary subbranch) of the letter "T" extends in a direction being perpendicular (thus, first primary angle is 90 degrees) to the bar (thus, the tangent to the first main path at the first primary connection). In the analogy used, since the bar of the letter "T" is a straight line, the tangent to the intersection (thus, the primary connection point) is coinciding with the bar as such. Likewise, the first secondary subbranch extends in a first secondary direction at a first secondary angle relative to a tangent to the first main path at the first secondary connection point.

In alternative embodiments, a given subbranch resembles a blot of conductive material being wider than the main branch and/or being displaced relative to a tangent to the first main path of the main branch. Thereby, rather than forming a "T"-like subbranch, the first primary subbranch may be a blot of conductive material generally extending in a first primary direction at a first primary angle relative to a tangent to the first main path at the first primary connection point. Thus, whereas subbranches as disclosed herein mainly relate to "T"-shaped subbranches, it is to be understood that the subbranches may likewise be provided in alternative shapes without departing from the scope.

In embodiments, the first primary angle and the first secondary angle are equal. In embodiments, the first primary angle and the first secondary angle differ. In an embodiment, the first primary angle and the first secondary angle are 90 degrees, each. In other words, in an embodiment, the first primary subbranch and the first secondary subbranch are perpendicular to the first main path of the first main branch of the first electrode. In embodiments, the first primary subbranch and the first secondary subbranch are symmetrical about a line of symmetry parallel with the first primary direction (as defined by the first primary angle) and the first secondary direction (as defined by the first secondary angle), respectively. Thereby, a load applied in such first primary direction and first secondary directions will exert an even force on the respective subbranch, such that a possible rupture of a subbranch is more uniform and consistent. In embodiments, the first primary and secondary angles are between 0 and 180 degrees, each. In embodiments, the first primary and secondary angles are >0 degrees and <180 degrees (thus, excluding subbranches being parallel with the first main branch), i.e. the first primary and secondary angles are selected from the interval]0; 180[degrees, such that the first primary subbranch and first secondary subbranch are non-parallel with the first main path of the first main branch at their respective first primary and secondary connection points. In embodiments, the first primary angle is selected from the interval]0; 180[degrees and the first secondary angle is selected from the interval]180; 360[degrees, such that the first primary and secondary subbranches may extend away from the first main branch on both sides of said first main branch, such as extend in opposite directions (e.g. such that the first primary angle is 90 degrees (i.e., perpendicular to the first main path on a first side of the first main branch) and the first secondary angle is 270 degrees (i.e., perpendicular to the first main path on a second side of the first main branch)).

In an embodiment, the first primary subbranch comprises a first primary sensing part and a first primary stem connecting the first main branch and the first primary sensing part, and the first secondary subbranch comprises a first secondary sensing part and a first secondary stem connecting the first main branch and the first secondary sensing part.

Thus, in embodiments, each of the subbranches, or at least the first primary subbranch and the first secondary subbranch, comprises a stem and a sensing part. For example, a sensing part can be considered a part of the subbranch being suitable for sensing, e.g. liquid, such as liquid content, and/or output, such as output resulting from a leakage, or an imminent leakage. The sensing part can be suitable for sensing e.g. by its shape, said shape potentially being annular, circular, oval, or rectangular. For example, the sensing part can be a circular dot or ring/annular, such that liquid content can come into contact with the sensing part. In embodiments, the sensing part has a maximum diameter or diagonal being less than 5 mm, such as less than 3 mm, such as 2 mm or 1 mm. The stem connects the sensing part and the main branch.

In an embodiment, the first main branch has a width being larger than a width of the first primary stem and a width of the first secondary stem. Thus, the width of the stem of a given subbranch may be less than the width of the main branch, such as to purposively reduce a tensile strength of the stem compared to a tensile strength of the main branch, such as to introduce a built-in tendency of the stem to rupture before the main branch when the electrode as such is exposed to handling/stretching. For the same reasons, in embodiments, the stem has a thickness being less than a thickness of the main branch. In embodiments, the width and/or thickness is varied by means of adequately controlling a printing process of the electrodes, such that the width and/or thickness is reflected in the deposited conductive ink according to the printing process. In embodiments, the stem has a width being less than 5 mm, such as less than 3 mm, such as 2 mm, 1 mm, or 0.5 mm.

In embodiments, the stem has a length between 2 mm and 15 mm, such as between 3 mm and 10 mm, such as 3 mm, 4 mm, 5 mm, 6 mm, 7 mm, 8 mm, 9 mm, or 10 mm. The length of the stem may be defined as the distance from the connection point to the sensing part of the given subbranch. In embodiments, the first primary and/or secondary stem has a width being equal to a width of the first main branch.

In embodiments, each subbranch of the plurality of subbranches has a length between 2 mm and 15 mm, such as between 3 mm and 10 mm, such as 3 mm, 4 mm, 5 mm, 6 mm, 7 mm, 8 mm, 9 mm, or 10 mm.

In embodiments, the subbranches of the first plurality of subbranches are distributed along the length of the first main branch. In embodiments, the subbranches are spaced apart by a fixed distance. In embodiments, the subbranches are spaced apart by a distance (e.g., measured point-to-point/in bee-line) between 10 mm and 20 mm, such as between 12 mm and 16 mm, such as in particular 14 mm. The distance may be measured from a connection point of a first primary subbranch to a connection point of a neighbouring first secondary subbranch. Studies have found that a spacing between 12 mm and 16, such as in particular 14 mm, provides a balance between the amount/area of adhesive that is removed/displaced by the presence of sensor point openings of the adhesive (discussed in detail below) in communication with (e.g., the sensing parts of) the subbranches and the resolution required to detect a certain amount/area of output in the interface between the appliance and the skin surface. In other words, reducing the spacing too much may reduce the adhesive properties of the appliance, since this introduces more sensor point openings in the adhesive material, and increasing the spacing too much may allow output to pass by the electrodes without being detected at a sensor point, and as such cause unexpected leakage. Thus, a spacing between 12 mm and 16 mm, in particularly and preferably 14 mm, have been found to provide such as balance. As will be discussed in greater detail below, in embodiments, by providing alternating subbranches of a first electrode and a second electrode, the distance between any two subbranches may be halved to between 6 mm and 8 mm, in particular 7 mm.

In an embodiment, the first main path is circular about a centre point.

As previously introduced, the first main branch extends along a first main path, such that the first main path defines the overall shape, direction, and/or extent of the first electrode. According to the present embodiment, the first main path is circular about a centre point. For example, the circular first main path has a diameter between 20 mm and 150 mm, such as between 40 mm and 80 mm.

By providing a circular first main path, the first main branch of the first electrode is configured to surround an ostomy when the sensor assembly is arranged in an ostomy appliance, e.g. a base plate or a sensor patch having a stomal opening with a centre point. Thus, the centre point of the first main path may be coinciding with the centre point of a base plate or a sensor patch when the sensor assembly is arranged/layered with such a base plate or sensor patch. Thereby, the first electrode may be configured for sensing at least part of the peristomal skin surface about an ostomy. In embodiments, the first main path is an arc of a circle having a centre point. For example, the first electrode comprising the first main branch extending along the first main path being an arc may cover a segment/angle space of between 90 degrees and 180 degrees, such as 120 degrees about the ostomy, such as to define a first sensing zone. In embodiments, a second and third electrode of the electrode assembly may define complimentary arcs of the circle, such as to provide a second and third sensing zone, each spanning an angle of 120 degrees, thereby providing three separate sensing zones about the ostomy.

According to previous embodiments, the first primary and secondary subbranches extend at a first primary and secondary angle relative to a tangent to the first main path at the first primary and secondary connection points, respectively. In further embodiments, the first primary and secondary angles are 90 degrees. Accordingly, when the first main path is circular about a centre point, or is an arc of a circle having such a centre point, the first primary and secondary subbranches may extend in radial direction of/from the centre point. In other words, since the first main path is circular about a centre point, or is an arc of a circle having such a centre point, a tangent to the first main path at a given connection point along the first main branch is perpendicular to the radial direction of/from the centre pint (i.e., the tangential direction is perpendicular to the radial direction).

A user handling a base plate and/or sensor patch having stomal opening is likely to stretch said base plate and/or sensor patch in the radial direction from a centre point thereof, such as to fit the base plate and/or sensor patch about his/her stoma. Thus, a sensor assembly provided in such a base plate and/or sensor patch is likely to be exposed to an elongation/stretch in the radial direction. By providing subbranches extending in the radial direction, it becomes more plausible that one or more of the subbranches of the first electrode ruptures than that the first main branch of said first electrode, namely because the former extends in the radial direction, whereas the latter extends circularly about the stoma. Thereby, the functionality of the first electrode is not compromised, but rather only the functionality of the given ruptured subbranch.

In an embodiment, the sensor assembly further comprises an insulative masking layer comprising a plurality of openings including a primary opening and a secondary opening. The electrode assembly is arranged between the support layer and the masking layer. In an embodiment, the primary opening coincides with the first primary sensing part and the secondary opening coincides with the first secondary sensing part.

By insulative is meant at least electrically insulative, such that the masking layer can electrically insulate at least parts of the electrode assembly, such as at least parts of the first electrode, such as the first main branch, from external exposure to fluids. For example, where the sensor assembly is layered with a base plate or a sensor patch, and where the support layer is likewise electrically insulative, the masking layer may define a series of sensor points where fluid may get in contact with exposed portions of the first electrode. According to an embodiment of the invention, the masking layer comprises a plurality of openings including a primary opening and a secondary opening. By an opening is meant an aperture or through-going opening of the masking layer allowing for the passage of fluids, such as liquid, such as stomal output. Further, according to the embodiment of the invention, the electrode assembly is arranged between the support layer and the masking layer. Thus, the electrode assembly is sandwiched between the insulative support layer and masking layer. Further, according to an embodiment, the primary opening coincides/is aligned with the first primary sensing part and the secondary opening coincides/is aligned with the first secondary sensing part. Thus, the plurality of openings of the masking layer exposes the sensing parts of the subbranches. Thereby, the plurality of openings of the masking layer allows for the sensing parts of the subbranches to be exposed to fluids, such as liquid, such as stomal output. Exposing the sensing parts of the subbranches allows for the generation of an electrical signal indicative of the presence of such fluid, liquid, or stomal output.

In embodiments, where the sensor assembly is layered with a base plate or a sensor patch comprising an adhesive layer comprising a plurality of through-going sensor point openings, said sensor point openings may be configured to overlap the sensing parts of the subbranches, e.g. to form a sensor point. In embodiments, the sensor point openings extend entirely through the adhesive layer of the base plate or sensor patch, such as to expose sensing parts of the subbranches of the first electrode to the surroundings, such as to provide means for establishing a short-circuit between the first and a second electrode comprising similar features, a short-circuit being indicative of a presence of liquid, such as output, on the proximal surface of the base plate. Thus, in embodiments, the sensor point openings provide means for detecting the presence of liquid on the proximal surface of the base plate by monitoring the voltage across two electrodes of the electrode assembly. The presence of liquid on the proximal surface of the base plate may be indicative of output propagating in the interface between the proximal surface of the base plate and the peristomal skin surface of a user.

In embodiments, the masking layer is bonded to the support layer, such as to a surface of the support layer, such as to the proximal and/or distal surface of the support layer. By being bonded is meant that in regions of the bond, the masking layer and the support layer move/stretch together when stretched. Thus, the bond provides that the masking layer can carry a load (stretch) applied to the sensor assembly, e.g. the base plate or sensor patch comprising the sensor assembly, thereby alleviating the effect (e.g. rupture or plastic deformation) the load can cause the support layer and/or electrode assembly provided thereupon. Thus, in embodiments, the masking layer can also be considered a reinforcement layer, such as reinforcing at least parts of the electrode assembly, such as at least parts of the first electrode, such as the first main branch.

In general, depending on the properties of the support layer and/or adhesive layer, e.g. an adhesive layer of the sensor assembly as such, a base plate or sensor patch comprising the sensor assembly, the elasticity of the support layer and/or adhesive layer can exceed the elasticity of the one or more electrodes (conductive traces), such as the first electrode, of the electrode assembly. In other words, the one or more electrodes, especially when printed, can be less elastic than the support layer and/or the adhesive layer. Thereby, the risk of overstretching and thus rupturing the electrodes arises during handling of the base plate or sensor patch. However, by providing a flexible masking layer in the base plate, such as bonded to a surface of the support layer, the elasticity of the support layer and/or adhesive layer can be reduced to a point where overstretching of the electrodes is inhibited, or where the risk is greatly reduced. Thus, in embodiments, the elasticity of the masking layer is less than the elasticity of the one or more electrodes of the electrode assembly, and/or the elasticity of the support layer, and/or the elasticity of the adhesive layer. Thereby, the masking layer becomes a limiting component of the sensor assembly in terms of elasticity, thereby reducing the overall elasticity in at least regions of the sensor assembly, such that the electrodes of the sensor assembly cannot be overstretched and thus rupture. In other words, in an embodiment, the masking layer inhibits overstretching the one or more electrodes of the electrode assembly. In embodiments, the masking layer is arranged according to a predefined pattern. In embodiments, the predefined pattern is designed to inhibit overstretching of the at least one electrode of the electrode assembly and/or to electrically insulate/mask at least parts of the at least one electrode from the adhesive layer, such as to define a series of exposed sensing parts as previously disclosed.

By elasticity is meant a material's ability to return to its original shape after a load, such as a uniaxial load, is removed (also known as elastic deformation). By having a high elasticity is meant that a material is capable of being stretched to a large extend before breaking and/or experiencing plastic deformation compared to a material having a low elasticity. In embodiments, the elasticity can be expressed in terms of Young's modulus E, generally expressed by:

$$E = \frac{\sigma(\varepsilon)}{\varepsilon} = \frac{FL_0}{A\Delta L},$$

where $\sigma(\varepsilon)$ is the tensile stress and $\varepsilon$ is the engineering extensional strain in the elastic portion of the physical stress-strain curve, and where F is the force exerted on an object under tension, Lo is the original length of the object, A is the actual cross-sectional area, which equals the area of the cross-section perpendicular to the applied force, and $\Delta L$ is the amount by which the length of the object changes. In embodiments, the masking layer has a Young's modulus being greater than the Young's modulus of the support layer and/or the one or more electrodes of the electrode assembly. Thereby is provided that a greater force is required to stretch and deform and/or break the masking layer than the support layer and/or the one or more electrodes provided thereupon. Thereby, the masking layer can withstand greater forces and thereby delimit the stretching of the support layer and consequently the electrode assembly provided thereupon. Thus, the masking layer carries a load applied to the sensor assembly (or base plate or sensor patch comprising the sensor assembly), rather than the one or more electrodes, the support layer, or an adhesive layer doing so.

Thereby, the masking layer, when serving to reinforce at least parts of the electrode assembly, further reduces the risk of compromising the functionality of the first electrode. For example, the masking layer is arranged according to a predefined pattern comprising the plurality of openings including the primary opening and the secondary opening configured to coincide with sensing parts of the first primary subbranch and the first secondary subbranch, respectively. Further, the masking layer may be absent or relatively thinner in areas of the stem of each of the plurality of subbranches, such as to purposively weaken the (vicinity of the) stems of the subbranches. By purposively weakening the vicinity of the stems of the subbranches, the chances of rupturing a subbranch is greater than the risk of rupturing the first main branch, where the former would merely compromise the functionality of the given subbranch, while the latter would result in the entire first electrode being compromised.

In embodiments, the masking layer comprises at least 10 openings, such as between 20 and 50 openings, in order to provide adequate leakage detection around the stoma of the user. In embodiments, the openings have a diameter of at least 1 mm, such as between 1.0 mm and 4.0 mm. In embodiments, the number of openings in the masking layer corresponds to the number of subbranches, and thus sensing parts, of electrodes of the electrode assembly. In embodiments, the masking layer has a thickness being less than 0.5 mm, such as less than 0.1 mm.

In embodiments, the masking layer is a lacquer. For example, the lacquer can be deposited in a predefined pattern on a surface of the support layer and electrode assembly arranged thereupon and subsequently cured/hardened to achieve the properties of the reinforcement layer as disclosed herein. Afterwards, the combined support layer, electrode assembly, and masking layer can be arranged adjacent to a distal surface of an adhesive layer of a base plate or a sensor patch. Thereby is provided a way of arranging a masking layer on the support layer. In embodiments, the lacquer is an acrylate lacquer, such as a UV curable acrylate lacquer. In alternative embodiments, other types of lacquers may be used, such as chemically curable lacquers and heat curable lacquers.

In an embodiment, the sensor assembly further comprises an adhesive layer with a proximal side configured for attachment of the sensor assembly to the skin surface of a user, the adhesive layer having a stomal opening. In embodiments, the electrode assembly is arranged on a proximal side of the support layer and the adhesive layer is arranged on a proximal side of the electrode assembly. In embodiments where the sensor assembly further comprises a masking layer, said masking layer is arranged on a proximal side of the electrode assembly, and the adhesive layer is arranged on a proximal side of the masking layer, such that a proximal surface of the adhesive layer is a proximal surface of the sensor assembly. In embodiments, the adhesive layer is a first adhesive layer made of a first composition as previously disclosed. In embodiments, the adhesive layer comprises a plurality of sensor point openings, as described above, configured to coincide with/overlap a plurality of openings of a masking layer and/or the sensing parts of the subbranches of the first electrode of the electrode assembly of the sensor assembly. Thereby, the sensor assembly according to the present embodiment may be considered the previously disclosed sensor patch configured for attachment to a base plate. Thus, in embodiments, the sensor assembly further comprising an adhesive layer is a sensor patch configured for attachment to an adhesive surface of a base plate, such as to provide said base plate with the sensing abilities as disclosed herein.

In an embodiment, the electrode assembly further comprises a second electrode. The second electrode comprises a second main branch extending along a second main path and a second plurality of subbranches connected to the second main branch, the second plurality of subbranches including a second primary subbranch and a second secondary subbranch. Thus, in embodiments, the second electrode of the electrode assembly may be considered structurally identical to the first electrode, or at least share some structural features. Thus, the features as disclosed in relation to the first electrode are considered applicable to the second electrode as well.

In embodiments, the second primary subbranch is connected to the second main branch at a second primary connection point and extending in a second primary direction at a second primary angle relative to a tangent to the second main path at the second primary connection point, and the second secondary subbranch is connected to the second main branch at a second secondary connection point and extending in a second secondary direction at a second secondary angle relative to a tangent to the second main path at the second secondary connection point.

In embodiments, the electrode assembly further comprises a third, a fourth, a fifth, or a sixth electrode, all of which may comprise features similar to those described in relation to the first and/or second electrode.

Providing at least two electrodes including the first electrode and the second electrode having the features as disclosed allows for applying a voltage across the electrodes, thereby facilitating determining electrical properties, such as resistance, of a medium, e.g. an adhesive layer and/or fluid, in contact with said electrodes. In particular, where the first and second electrodes comprise the features as disclosed herein, the risk of compromising one or both of said electrodes due to rupturing is reduced for the reasons as disclosed in relation to the first electrode.

In an embodiment, the first main branch and the second main branch are substantially parallel.

Thus, the distance between the first main branch and the second main branch is constant. Thereby, electrical properties determined from applying a voltage across first and second electrode may be easily comparable and/or reproducible. In embodiments, the distance between the first main branch and the second main branch is less than 50 mm, such as less than 30 mm, such as less than 10 mm, such as between 1 mm and 10 mm.

In embodiments, the first main branch and the second main branch are circular about a centre point, such as circular about the centre point as previously disclosed in relation to the first electrode. In embodiments, the first main branch and the second main branch are concentric about the centre point. Thus, in embodiments, the first main branch is arranged at a first radial distance from the centre point, and the second main branch is arranged a second radial distance from the centre point, the second radial distance being greater than the first radial distance. Thus, even when being circular, the first and second main branches may be parallel. Thereby is provided a circular sensor, such as a sensor configured to monitor the peristomal skin surface about an ostomy.

In an embodiment, the first primary subbranch and the first secondary subbranch extend towards the second main branch of the second electrode, and the second primary subbranch and the second secondary subbranch extend towards the first main branch of the first electrode.

In embodiments, the second primary subbranch comprises a second primary sensing part and a second primary stem connecting the second main branch and the second primary sensing part, and the second secondary subbranch comprises a second secondary sensing part and a second secondary stem connecting the second main branch and the second secondary sensing part.

In embodiments, the first primary sensing part, the first secondary sensing part, the second primary sensing part, and the second secondary sensing part are aligned, such as to form a line of sensing parts (when viewed in a direction parallel to the first and/or second main path). In embodiments, such line of sensing parts may be considered imaginary. In embodiments, the line of sensing parts is alternating between a sensing part of a subbranch connected to the first main branch and a sensing part of a subbranch connected to the second main branch. Thereby, the rupture of a single subbranch (e.g. the first primary subbranch) does not compromise the sensing ability, or coverage thereof, of the electrode assembly as such, as there will always be a neighbouring subbranch (e.g. the first secondary subbranch) being adjacent a subbranch of the second electrode (e.g. the second primary subbranch). In other words, by having alternating subbranches, a coverage of sensing abilities may be considered optimised, i.e. the distance from a subbranch of the first electrode to a subbranch of the second electrode is at a minimum, irrespective of an actual distance between the subbranches as such. As was disclosed in relation to the first electrode, the distance between respective subbranches of a given electrode may be between 12 and 16 mm, such as 14 mm. By alternating between a subbranch of the first electrode and a subbranch of the second electrode, a distance between such two alternating subbranches is halved to between 6 mm and 8 mm, in particularly 7 mm. This is particularly relevant with regard to the risk of output passing by the electrodes undetected.

In a second aspect of the invention, a method of manufacturing a sensor assembly for an ostomy appliance is disclosed. The method comprises the steps of providing a support layer and printing with a conductive ink, on a surface of the support layer, an electrode assembly comprising at least a first electrode. The first electrode comprises a first main branch extending along a first main path and a first plurality of subbranches connected to the first main branch, the first plurality of subbranches including a first primary subbranch and a first secondary subbranch, wherein the first primary subbranch is connected to the first main branch at a first primary connection point and extending in a first primary direction at a first primary angle relative to a tangent to the first main path at the first primary connection point, and wherein the first secondary subbranch is connected to the first main branch at a first secondary connection point and extending in a first secondary direction at a first secondary angle relative to a tangent to the first main path at the first secondary connection point.

Embodiments and features relating to the first aspect of the invention are considered applicable to the second aspect of the invention as disclosed herein. In particular, structural features and layouts of the electrodes, including the main branches and the respective subbranches, are considered applicable to a method of manufacturing a sensor assembly comprising such features.

In embodiments, the method further comprises the step of providing an adhesive layer and layering the support layer with the electrode assembly with the adhesive layer. In embodiments, the electrode assembly as printed according to the second step of the method further comprises a second electrode, such as a second electrode according to embodiments of the first aspect of the invention. In embodiments, the method further comprises the step of providing, such as depositing, a masking layer on the electrode assembly and support layer according to a predefined pattern, the predefined pattern including at least openings of, such as lack of, masking layer on sensing parts of the subbranches of the first electrode, the sensing parts being sensing parts as disclosed in relation to the first aspect of the invention.

In a third aspect of the invention, a base plate for an ostomy appliance is disclosed. The base plate comprises a first adhesive layer with a proximal side configured for attachment of the base plate to the skin surface of a user, the first adhesive layer having a stomal opening, and a sensor assembly according to embodiments of the first aspect of the invention. The electrode assembly of the sensor assembly is arranged between a distal side of the first adhesive layer and the support layer of the sensor assembly.

Thus, the base plate comprises a sensor assembly as disclosed in relation to the first aspect of the invention. Thereby, the base plate may be provided with the sensing abilities as being provided by the sensor assembly as discussed throughout the present disclosure. For example, the base plate may be provided with such sensing abilities of the sensor assembly by means of coupling a monitor device to a monitor interface of the sensor assembly, such that said monitor device can collect data, such as ostomy data, from the electrodes of the sensor assembly. In embodiments, collecting ostomy data from the electrodes of the sensor assembly includes applying a voltage across at least two electrodes of the electrode assembly and monitoring the current, and thereby the resistance. For example, the resistance may be indicative of a moisture content in the first adhesive layer of the base plate, or the resistance may be indicative of the presence of liquid, such as stomal output, in the interface between the skin surface and the proximal side of the first adhesive layer.

DETAILED DESCRIPTION OF THE DRAWINGS

FIG. 1 illustrates an exemplary ostomy system. The ostomy system 1 comprises an ostomy appliance 2 including a base plate 10 according to the invention. The base plate 10 is adapted to support an ostomy pouch (not shown). Further, the ostomy system 1 comprises a monitor device 6 and an accessory device 8 (e.g., a mobile telephone). The monitor device 6 is connectable to the base plate 10 via respective first connectors of the monitor device 6 and base plate 10. The monitor device 6 is configured for wireless communication with the accessory device 8. Optionally, the accessory device 8 is configured to communicate with a server device 4 of the ostomy system 1, e.g. via network 9. The server device 4 may be operated and/or controlled by the ostomy appliance manufacturer and/or a service centre. Ostomy data or parameter data based on the ostomy data are obtained from electrodes/sensors of the ostomy appliance 2 with the monitor device 6. The monitor device 6 processes the ostomy data and/or parameter data based on the ostomy data. Based on the processed ostomy data, the monitor device 6 may determine what monitor data that are transmitted to the accessory device 8. In the illustrated ostomy system, the accessory device 8 is a mobile phone, however the accessory device 8 may be embodied as another handheld device, such as a tablet device, or a wearable, such as a watch or other wrist-worn electronic device. Accordingly, the monitor device 6 is configured to determine and transmit monitor data to the accessory device 8. The base plate 10 comprises a coupling member 5 in the form of a coupling ring 5' for coupling an ostomy pouch (not shown) to the base plate (two-part ostomy appliance). The base plate 10 has a stomal opening 13 with a centre point 13'. The size and/or shape of the stomal opening 13 is typically adjusted by the user or nurse before application of the ostomy appliance to accommodate the user's stoma. The base plate 10 comprises a sensor assembly comprising an electrode assembly.

The ostomy system 1 optionally comprises a docking station 20 forming an alternative/additional accessory device of the ostomy system 1. The docking station 20 comprises a docking monitor interface including a first connector 22 configured for electrically and/or mechanically connecting the monitor device 6 to the docking station 20. The docking monitor interface may be configured for wirelessly connecting the monitor device to the docking station. The docking station 20 comprises a user interface 24 for receiving user input and/or providing feedback to the user on the operational state of the docking station 20. The user interface 24 may comprise a touch-screen. The user interface 24 may comprise one or more physical buttons and/or one or more visual indicators, such as light emitting diodes.

Figure 2:
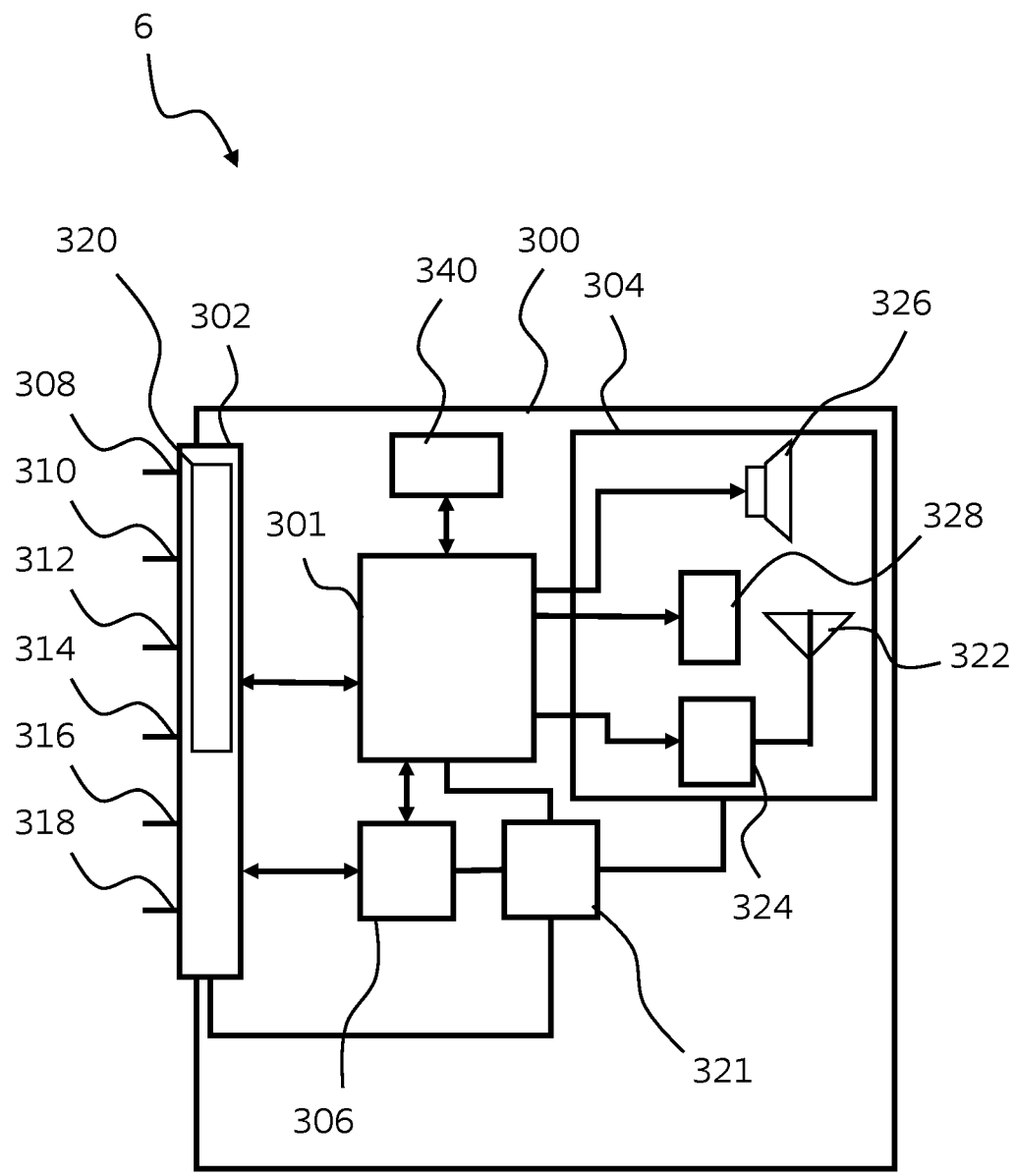
FIG. 2 illustrates a schematic block diagram of an exemplary monitor device.

FIG. 2 is a schematic block diagram of an exemplary monitor device 6. The monitor device 6 comprises a monitor device housing 300, a processor 301, and one or more interfaces, the one or more interfaces including a first interface 302 (appliance interface) and a second interface 304 (accessory interface). The monitor device 6 comprises a memory 306 for storing ostomy data and/or parameter data based on the ostomy data. The memory 306 is connected to the processor 301 and/or the first interface 302.

The first interface 302 is configured as an appliance interface for electrically and/or mechanically connecting the monitor device 6 to the ostomy appliance, e.g. ostomy appliance 2 of FIG. 1. The first interface 302 comprises a plurality of terminals for forming electrical connections with respective terminals of the ostomy appliance 2 (base plate 10, such as monitor interface 122 of FIG. 1). The first interface 302 comprises a ground terminal 308, a first terminal 310, a second terminal 312 and a third terminal 314. The first interface 302 optionally comprises a fourth terminal 316 and a fifth terminal 318. The first interface 302 of the monitor device 6 comprises a coupling part 320 for forming a mechanical connection, such as a releasable coupling between the monitor device and the base plate. The coupling part 320 and the terminals 308, 310, 312, 314, 316, and 318 of the first interface 302 form (at least part of) a first connector of the monitor device 6.

The monitor device 6 comprises a power unit 321 for powering the monitor device and active components thereof, i.e. the power unit 321 is connected to the processor 301, the first interface 302, the second interface 304, and memory 306. For example, the power unit 321 may be configured to apply a voltage across two or more electrodes of an electrode assembly. The power unit comprises a battery and charging circuitry. The charging circuitry is connected to the battery and terminals of the first interface 302 for charging the battery via terminals of the first interface, e.g. terminals of the first connector.

The second interface 304 of the monitor device is configured as an accessory interface for connecting the monitor device 6 to one or more accessory devices such as accessory device 8 of FIG. 1. The second interface 304 comprises an antenna 322 and a wireless transceiver 324 configured for wireless communication with accessory device(s). Optionally, the second interface 304 comprises a loudspeaker 326 and/or a haptic feedback element 328 for provision of respective audio signal and/or haptic feedback to the user.

The monitor device 6 optionally comprises a sensor unit 340 connected to the processor 301. For example, the sensor unit 340 comprises a temperature sensor for feeding temperature data to the processor and/or a G-sensor or accelerometer for feeding acceleration data to the processor 301. Additionally and/or alternatively, the sensor unit 340 comprises a humidity sensor and/or an acoustic sensor. The sensor unit 340 may comprise alternative and/or additional sensors suitable and/or relevant to an ostomy system as described.

The processor 301 is configured to apply a processing scheme, and the first interface 302 is configured for collecting ostomy data from the base plate and/or the sensor patch coupled to the first interface, such as from a sensor assembly of such a base plate and/or sensor patch, the ostomy data comprising first ostomy data from a first electrode pair of the base plate and/or the sensor patch, second ostomy data from a second electrode pair of the base plate and/or the sensor patch, and third ostomy data from a third electrode pair of the base plate and/or the sensor patch. The ostomy data may be stored in the memory 306 and/or processed in the processor 301 in order to obtain parameter data. The parameter data may be stored in the memory 306. The processor 301 is configured to apply a processing scheme, wherein to apply a processing scheme comprises obtain first parameter data based on the first ostomy data; obtain second parameter data based on the second ostomy data; obtain third parameter data based on the third ostomy data. In other words, the processor 301 is configured to obtain first, second and third parameter data based on respective first, second and third ostomy data. To apply a processing scheme comprises to determine an operating state of the base plate and/or the sensor patch of the ostomy appliance based on one or more, e.g. all, of the first parameter data, the second parameter data and the third parameter data, wherein the operating state is indicative of a degree of radial erosion of the base plate and/or the sensor patch and/or acute leakage risk for the ostomy appliance. The monitor device 6 is configured to, in accordance with a determination that the operating state is a first operating state, transmit a first monitor signal comprising monitor data indicative of the first operating state of the base plate and/or the sensor patch via the second interface; and in accordance with a determination that the operating state is a second operating state, transmit a second monitor signal comprising monitor data indicative of the second operating state of the base plate and/or the sensor patch via the second interface.

Figure 3:
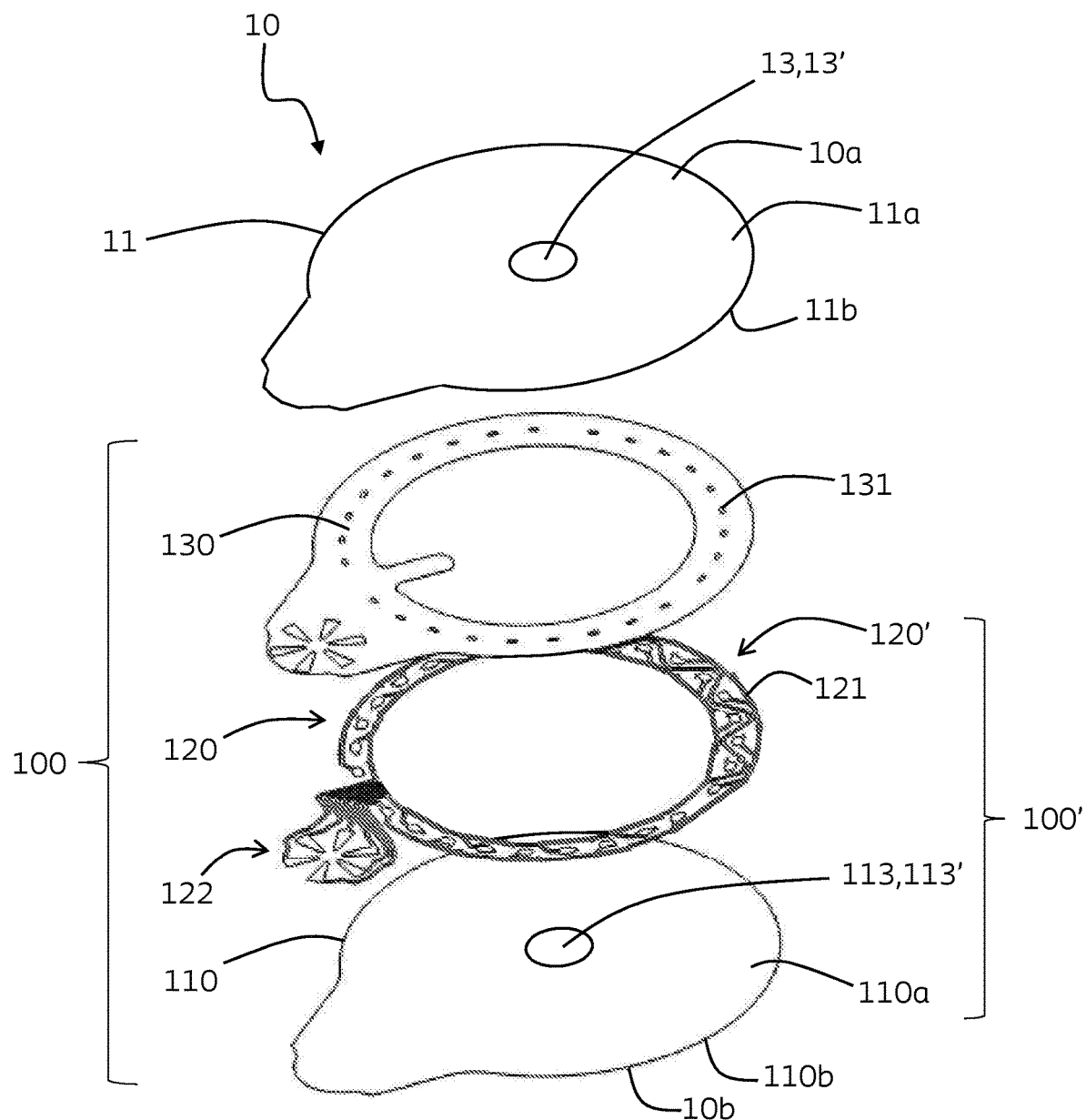
FIG. 3 illustrates an exploded view of an ostomy appliance comprising a sensor assembly according to an embodiment of the invention.

FIG. 3 illustrates an exploded view of an ostomy appliance, such as a base plate 10, comprising a sensor assembly 100 according to an embodiment of the invention. Whereas the present discussion relates to the base plate 10, the discussion may instead relate to a sensor patch configured for attachment to a proximal surface of a base plate.

The base plate 10 comprises a first adhesive layer 11 and a sensor assembly 100 comprising a support layer 110, an electrode assembly 120, and a masking layer 130. In alternative embodiments of the invention, the masking layer 130 is omitted from the sensor assembly 100, whereby the base plate 10 comprises the first adhesive layer 11 and a sensor assembly 100' comprising the electrode assembly 120 and the support layer 110.

The first adhesive layer 11 comprises a proximal surface 11a, a distal surface 11b, and a stomal opening 13 with a centre point 13'. The proximal surface 11a of the first adhesive layer 11 is adapted for attachment to a skin surface of a user, e.g. after removal of a protective release liner (not shown). Thus, the proximal surface 11a of the first adhesive layer 11 may double as the proximal surface 10a of the assembled base plate 10 as such.

The support layer 110 of the sensor assembly 100,100' comprises a proximal surface 110a, a distal surface 110b, and a stomal opening 113 with a centre point 113' coinciding with the centre point 13' of the first adhesive layer 11. The distal surface 110b of the support layer 110 may double as the distal surface 10b of the assembled base plate 10.

The electrode assembly 120 comprises at least a first electrode 121, e.g. a plurality of electrodes 120', and a monitor interface 122 allowing for an electrical connection between the at least first electrode 121, such as the plurality of electrodes 120', and a monitor device couplable to the monitor interface. Thus, the monitor interface 122 is configured for electrically and/or mechanically connecting the ostomy appliance (base plate 10) to the monitor device. The monitor interface of the base plate comprises a coupling part (not shown) for forming a mechanical connection, such as a releasable coupling between the monitor device and the base plate 10. The coupling part is configured to engage with a corresponding coupling part of the monitor device for releasably coupling the monitor device to the base plate 10. Further, the monitor interface 122 comprises a plurality of terminal elements respectively forming a plurality of terminals for forming electrical connections between at least the first electrode 121 and respective terminals of the monitor device. Details in relation to the electrode assembly 120 and in particular in relation to the first electrode 121 will be discussed further in relation to FIGS. 5-9.

The masking layer 130 is arranged on the proximal side and/or surface 110a of the support layer 110, such that the masking layer 130 covers at least parts of the electrode assembly 120, whereby said parts of the electrode assembly 120 are sandwiched between the masking layer 130 and the support layer 110. Thereby, the masking layer 130, being electrically insulative, may insulate the at least parts of the electrode assembly 120 from moisture and/or fluids and further inhibit overstretching of the electrodes 120'. Further, the illustrated masking layer 130 comprises a plurality of openings 131 exposing sensing parts of the electrodes 120', in particular exposing said sensing parts to the distal surface 11b of the first adhesive layer 110. The plurality of openings 131 allows for manipulating how and where electrical measurements of the first adhesive layer 110 are made by means of the plurality of electrodes 120'.

The base plate 10 according to FIG. 3 may comprise further features, including, but not limited to, a second adhesive layer, a top film defining a distal surface of the base plate 10, where the support layer of the sensor assembly 100,100' is not a top film, a release liner protecting the first and/or second adhesive layer, and a first intermediate element arranged on the proximal side of the electrode assembly, between the terminal elements forming terminals and the first adhesive layer. The first intermediate element may cover the terminal elements forming terminals and protect the first adhesive layer from mechanical stress from the terminal elements of the base plate.

Figure 4:
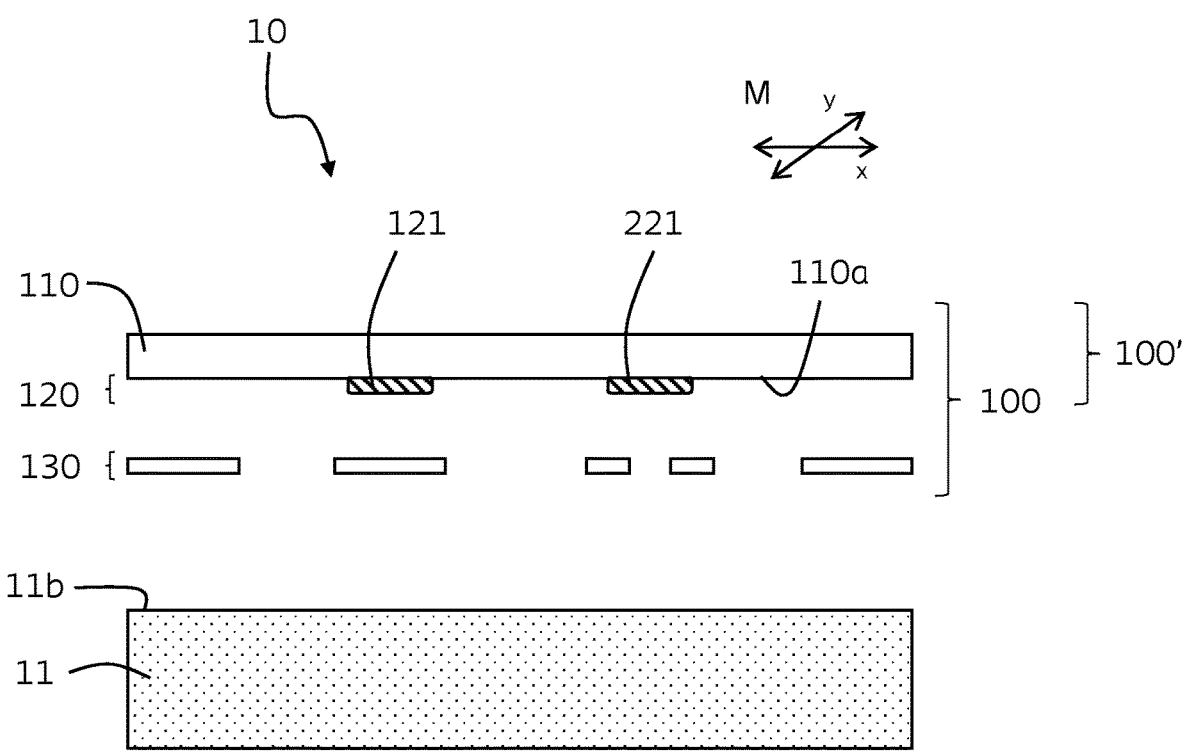
FIG. 4 illustrates an exploded cross-sectional view of a segment of an ostomy appliance comprising a sensor assembly according to embodiments of the invention.

FIG. 4 illustrates an exploded cross-sectional view of a segment of an ostomy appliance, such as a base plate 10, comprising a sensor assembly 100 according to embodiments of the invention. The embodiment of FIG. 4 may be considered a cross-sectional view of a segment of the ostomy appliance, such as the base plate 10, of FIG. 3. The cross-sectional view of FIG. 4 may be a cross-sectional view of a sensor patch.

The base plate 10 comprises a first adhesive layer 11 and a sensor assembly 100 comprising a support layer 110, an electrode assembly 120 (not to scale), and a masking layer 130. In alternative embodiments of the invention, the masking layer 130 is omitted from the sensor assembly 100, whereby the base plate 10 comprises the first adhesive layer 11 and a sensor assembly 100' comprising the electrode assembly 120, and the support layer 110. The masking layer 130 is arranged between the proximal surface 110a of the support layer 110 and a distal surface 11b of the first adhesive layer 11. The masking layer 130 is bonded to the proximal surface 110a of the support layer 110 in an assembled embodiment, whereby the masking layer 130 is able to insulate at least parts (examples shown) of the electrodes 121,221 of the electrode assembly 120, and potentially to carry a load applied to the support layer 110 and/or base plate 10 as such. In particular, the masking layer 130 may be able to carry a load in the directions indicated by the coordinate system M (thus, the directions being parallel to the extent of the base plate). The masking layer 130 insulates the electrodes 121,221 from moisture and/or liquid, such as to avoid unintentional short-circuiting; and may, depending on material properties, inhibit overstretching of the electrodes 121,221 by carrying the load. The masking layer 130 may have a Young's modulus being greater than a Young's modulus of support layer 110, and/or the electrode assembly 120, and/or the first adhesive layer 11, whereby the masking layer 130 limits the overall elasticity of the base plate 11 to a point where overstretching the electrodes 121,221 is (greatly) reduced, such as inhibited. Thereby, along with the structural features (not shown) of the electrodes 121,221 as such, as will be discussed in greater detail below, the masking layer 130 may further reduce the risk of rupturing the electrodes 121,221 of the electrode assembly 120.

Figure 5A:
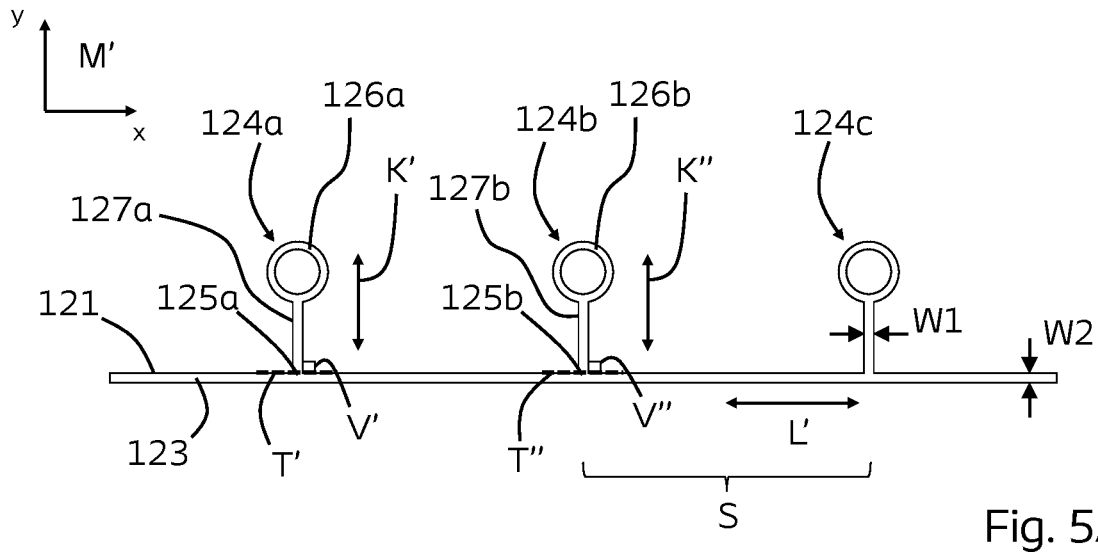
FIG. 5A illustrates a segment of a first electrode of a sensor assembly according to an embodiment of the invention.
Figure 5B:
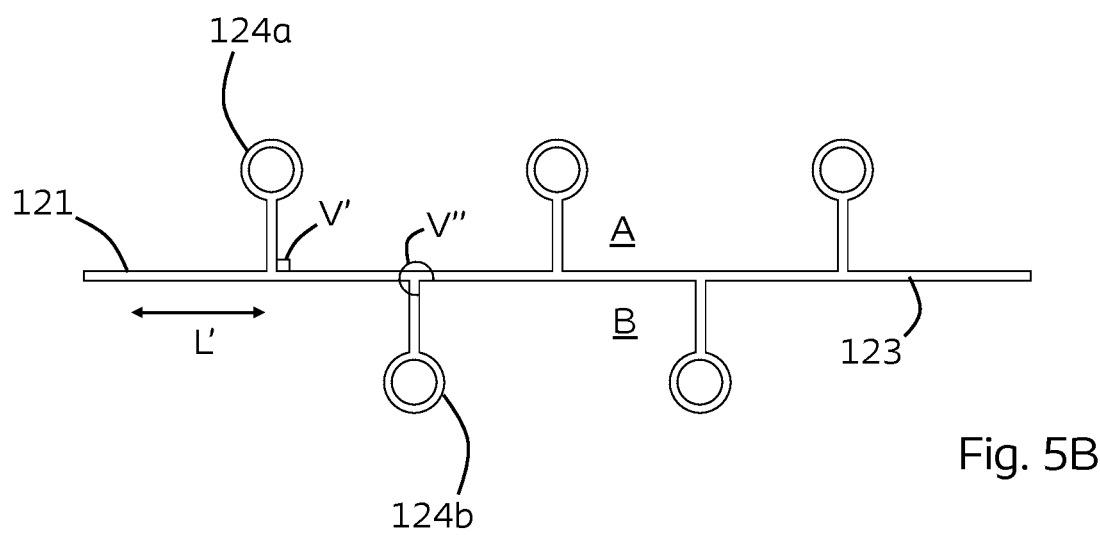
FIG. 5B illustrates a segment of a first electrode of a sensor assembly according to an embodiment of the invention.
Figure 5C:
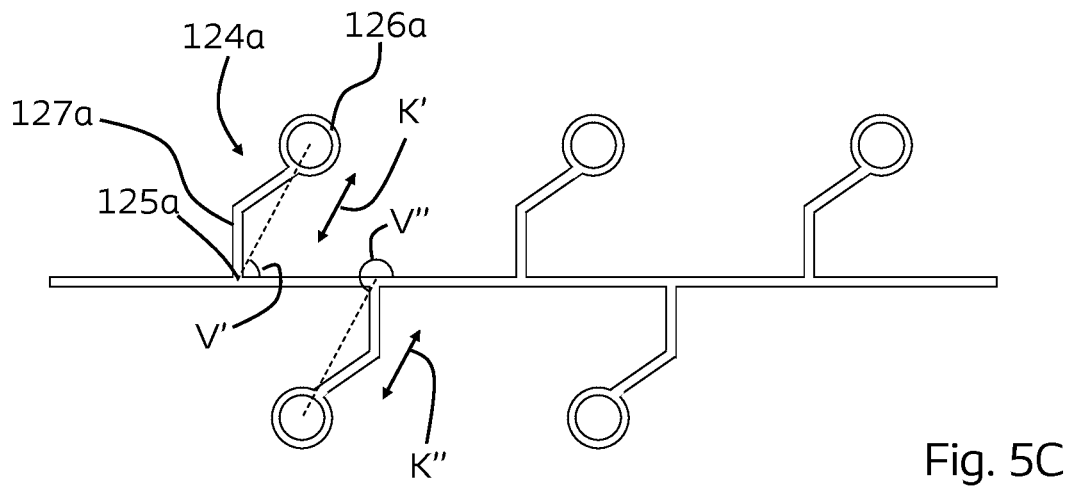
FIG. 5C illustrates a segment of a first electrode of a sensor assembly according to an embodiment of the invention.

FIGS. 5A-C illustrate different embodiments of a first electrode 121 of a planar electrode assembly according to embodiments of the invention. By planar is meant that when considering a direction and/or angle relative to a certain feature, the direction and/or angle span a two-dimensional geometric plane (x,y) as indicated by the coordinate system M' of FIG. 5A, inserted for clarity. In particular, the coordinate system M' complies with the coordinate system M of FIG. 4.

FIG. 5A illustrates a segment of a first electrode 121 comprising a first main branch 123 extending along a first main path L'. Further, the first electrode 121 comprises a first plurality of subbranches 124a,124b,124c, including a first primary subbranch 124a, a first secondary subbranch 124b, and a first tertiary subbranch 124c. In the following, mainly the first primary subbranch 124a and the first secondary subbranch 124b will be considered, where it is understood that further subbranches, such as the first tertiary subbranch 124c, may exhibit like features. The first primary subbranch 124a is connected to the first main branch 123 at a first primary connection point 125a and extending in a first primary direction K' at a first primary angle V' relative to a tangent T' (bold, dashed line) to the first main path L' at the first primary connection point 125a. Likewise, the first secondary subbranch 124b is connected to the first main branch 123 at a first secondary connection point 125b and extending in a first secondary direction K" at a first secondary angle V" relative to a tangent T" (bold, dashed line) to the first main path L' at the first secondary connection point 125b. According to the illustrated embodiment, the first main path L' is a straight line, meaning that the tangents T',T" to the first main path L' at the first primary 125a and secondary connection point 125b are parallel with, and coinciding with, said first main path L'. In embodiments, the first main path L' may comprise a curvature, e.g. where the first main branch 123 is circular, whereby the tangent to the first main path L' at a given connection point is clearer. This is illustrated in FIG. 7.

In preferred embodiments, the subbranches 124a,124b, 124c are integral with the first main branch 123, e.g. formed in a single process, such as printed in a single process, such that the subbranches 124a,12b,124c and the first main branch 123 are continuous/unbroken. In the embodiment of FIG. 5A, each of the first primary angle V' and the first secondary angle V" are equal and 90 degrees, such that the first primary direction K' and first secondary direction K" are perpendicular to the first main branch 123 at their respective connection points 125a,125b. In alternative embodiments, the first primary angle V' is different from the first secondary angle V" or both being equal but different from 90 degrees.

In embodiments, as illustrated in FIG. 5A, the subbranches 124a,124b,124c may be symmetric about a line of symmetry parallel with their respective first primary direction K' and first secondary direction K". Thereby, a load applied in such first primary direction K' and first secondary directions K" will exert an even force on the respective subbranch, such that a possible rupture of a subbranch is more uniform and consistent.

According to the illustrated embodiment, the first primary subbranch 124a comprises a first primary sensing part 126a and a first primary stem 127a connecting the first main branch 123 and the first primary sensing part 126a. Likewise, the first secondary subbranch 124b comprises a first secondary sensing part 126b and a first secondary stem 127b connecting the first main branch 123 and the first secondary sensing part 126b. The sensing parts 126a,126b may be annular/ring-shaped as illustrated, or they may be circular, rectangular, or any other suitable shape. The sensing parts 126a,126b are bigger in size (e.g., diameter) than a width of the corresponding stem 127a,127b, such that the sensing parts 126a,126b may more easily be exposed to the surroundings, such as to provide a certain surface for a medium to get into contact with the respective sensing part. In embodiments, the stems 127a,127b may have a width W1 (indicated for the first tertiary subbranch 124c) being less than a width W2 of the first main branch 123, thereby providing a comparably weaker link.

The subbranches 124a,124b facilitate that a functionality (e.g., ability to conduct a current/signal) of the first electrode 121 is not compromised due to a rupture of one or more of the subbranches 124a,124b. In particular, where a stretch is expected in the first primary K' and/or secondary direction K", such as due to a user handling a sensor assembly comprising the electrode assembly and thus the first electrode 121, one or more of the subbranches 124a,124b are more likely to rupture (become disconnected) from the first main branch 123. However, due to the provision of the subbranches 124a,124b and their mutual independency, one or more ruptured subbranches 124a,124b do not greatly compromise the remaining subbranches and/or the first main branch 123 as such. In other words, a rupture of one or more subbranches 124a,124b does not compromise the ability to conduct a signal through the first main branch 123 and thus the first electrode 121 as such. By providing a stem having a width being less than a width of the first main branch 123, the subbranches are even more likely to rupture before the first main branch 123. Thus, by providing a narrow stem, a weak link is purposively provided.

Whereas the distance S between each of the subbranches 124a,124b,124c is constant according to the illustrated embodiment, it is foreseen that such a distance S may vary. In embodiments, the distance S between each of the subbranches 124a,124b,124c is between 5 mm and 30 mm, such as between 8 mm and 20 mm, such as between 12 mm and 16 mm, such as 14 mm.

FIG. 5B illustrates a segment of a first electrode 121 comprising a first main branch 123 extending along a first main path L'. Here, subbranches are arranged on both sides of the first main branch 123, such that a first primary subbranch 124a is arranged on a first side A of the first main branch 123 and a first secondary subbranch 124b is arranged on a second side B of the first main branch 123 (further subbranches not explicitly denominated for simplicity). The relationship between the first primary 124a and secondary subbranch 124b may be expressed in terms of the first primary angle V' and first secondary angle V'''. According to the illustrated embodiment, the first primary angle V' is 90 degrees relative to the first main path L' (tangent not illustrated as the first main path L' is a straight line), whereas the first secondary angle V''' is 270 degrees, relative to the same reference point as the first primary angle V', thereby forming a 90 degree angle (perpendicular) relative to the first main path L' on the second side B of the first main branch 123. Thus, in FIG. 5B, the first primary subbranch 124a and the first secondary subbranch 124b extend in opposite directions within the (x,y)-plane as previously defined.

In a preferred embodiment of the first electrode 121 of FIG. 5B, the plurality of subbranches are alternating between being arranged on the first side A and the second side B of the first main branch 123, such that, along the extent of the first electrode 121, both sides A,B are equally covered by subbranches of the first main branch 123.

A first electrode 121 according to FIG. 5B may be suitable for forming a first sensor with a second electrode on the first side A and a second sensor with a third electrode on the second side B, such that two sensors may be formed from three electrodes. Thus, the first electrode 121 according to FIG. 5B may be a common ground electrode forming ground (when a voltage is applied) for a second electrode and a third electrode.

FIG. 5C illustrates a segment of a first electrode 121 comprising a first main branch 123 extending along a first main path L'. Here, subbranches are arranged on both sides of the first main branch 123, as in FIG. 5B, but extending in directions K',K'' where the first primary V' and secondary angles V''' are different from 90 degrees. According to the illustrated embodiment, the first primary angle V' is calculated as the angle formed by the line (dashed) extending from the first primary connection point 125a to a centre of the first primary sensing part 126a relative to the first main branch 123, thus neglecting the course of the stem 127a, which may comprise bends as illustrated. Consequently, the first primary direction K' may be considered the direction between the first primary connection point 125a and a centre of the first primary sensing part 126. The features of the first primary subbranch 124a apply mutatis mutandis to the remaining subbranches of the first electrode 121 of FIG. 5C.

Figure 6:
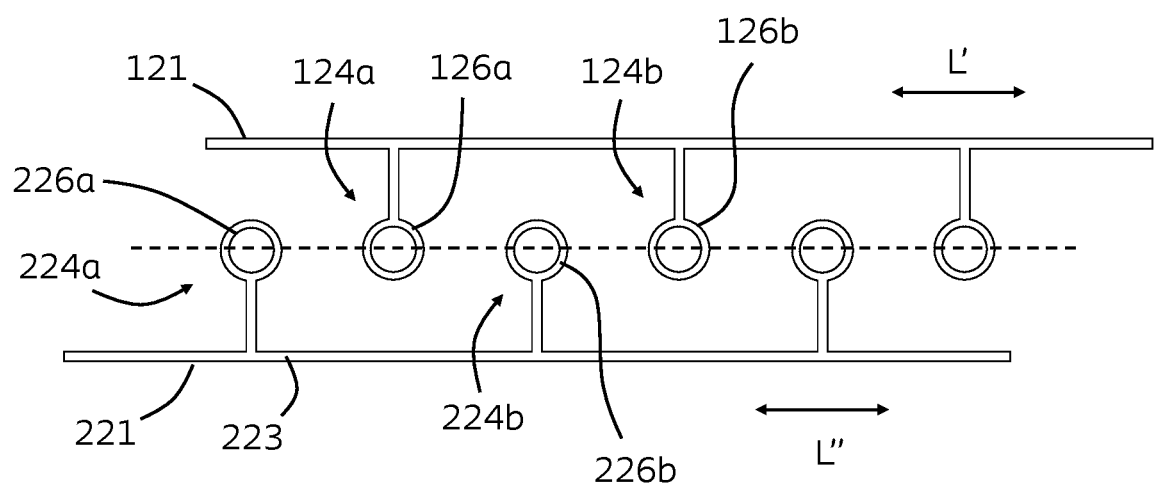
FIG. 6 illustrates a segment of a first and second electrode of a sensor assembly according to an embodiment of the invention.

FIG. 6 illustrates a segment of a first electrode 121, such as the first electrode as discussed in relation to FIG. 5A, and a second electrode 221 comprising features similar to the features of the first electrode 121: the second electrode 221 comprises a second main branch 223 extending along a second main path L'' and a second plurality of subbranches connected to the second main branch 223, the second plurality of subbranches including a second primary subbranch 224a and a second secondary subbranch 224b. According to the illustrated embodiment, the first main path L' of the first electrode 121 is parallel with the second main path L'' of the second electrode 221. Further, the first primary subbranch 124a and the first secondary subbranch 124b extend towards the second main branch 223, and the second primary subbranch 224a and the second secondary subbranch 224b extend towards the first main branch 123. In other words, the subbranches are arranged in a direction being perpendicular to the tangent to the first main path L',L'' at their respective connection points. Finally, according to the illustrated embodiment, the first primary sensing part 126a, the first secondary sensing part 126b, the second primary sensing part 226a, and the second secondary sensing part 226b are aligned, such as to form a (straight) line (dashed) of sensing parts, when seen in the direction of the first and second main path L,L'. Such line of sensing parts may be considered imaginary, as the sensing parts are not connected along this line as such, but the line serves to highlight how the first electrode 121 and the second electrode 221 are arranged relative to each other. As illustrated, the line of sensing parts may alternate between a sensing part of a subbranch connected to the first main branch 123 and a sensing part of a subbranch connected to the second main branch 223.

Figure 7A:
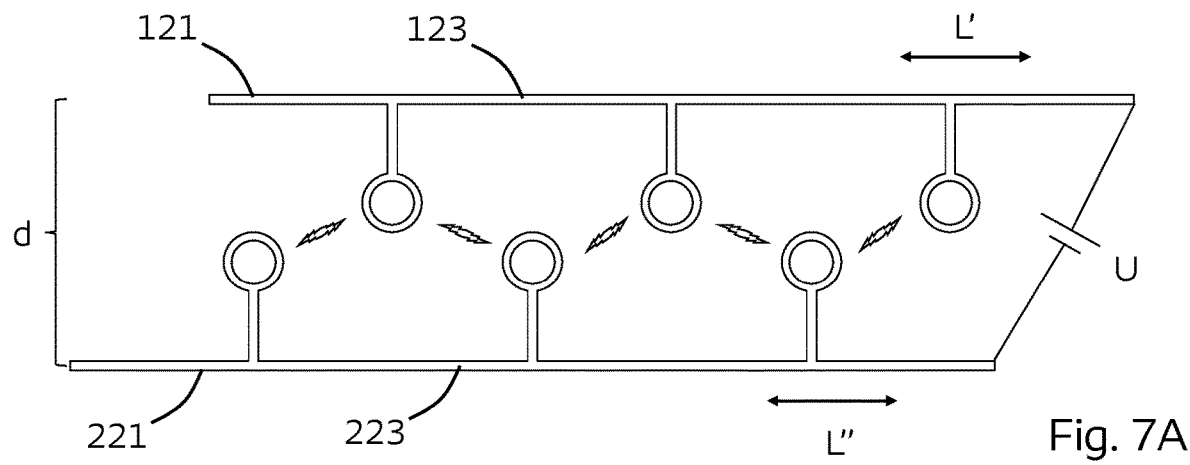
FIG. 7A illustrates a segment of a first and second electrode of a sensor assembly according to an embodiment of the invention.

FIG. 7A illustrates a segment of a first electrode 121 and a second electrode 221 being parallel, such as according to FIG. 6. Here, the first electrode 121 and the second electrode 221 are separated by a distance d being greater than a length of each of plurality of subbranches of each of the two electrodes 121,221, such that the sensing parts are not arranged on a straight line as in FIG. 6. Rather, the sensing parts, still alternating (when seen in the direction of the first and second main path L',L'') between a sensing part of a subbranch connected to the first main branch 123 and a sensing part of a subbranch connected to the second main branch 223, are arranged on a zigzag line (not explicitly indicated). By separating the first electrode 121 and the second electrode 221 farther, the electrodes 121,221 may form a sensor capable of measuring a larger area, namely the area between the electrodes. For example, where the electrodes 121,221 are layered with an adhesive layer of an ostomy appliance, such as a base plate or a sensor patch, the electrodes may form a sensor configured to determine a moisture content in the adhesive layer and/or the presence of fluids, such as liquid, such as stomal output, on a proximal side of the adhesive layer in the area defined by the distance d and an extent of the electrodes. In particular, the sensor may be configured to do so by applying a voltage U (ac or dc) as indicated. By applying a voltage U, electrical properties, such as resistance, may be assessed by considering the current conducted/flowing between the sensing parts, as indicated by arrows between each of the sensing parts.

Figure 7B:
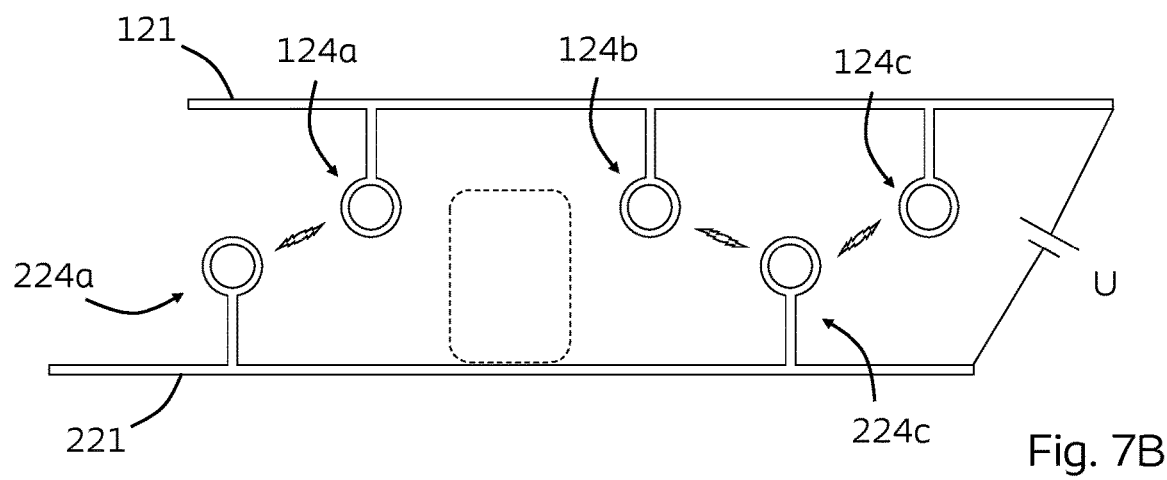
FIG. 7B illustrates a segment of a first and second electrode of a sensor assembly according to an embodiment of the invention.

FIG. 7B illustrates the situation where one of the subbranches of the second electrode 221 has been disconnected/ruptured from the second main branch 223 (indicated by a dashed box). For example, the ruptured subbranch is the second secondary subbranch. The illustrated segment of the first electrode 121 comprises a first primary subbranch 124a, a first secondary subbranch 124b, and a first tertiary subbranch 124c, while the second electrode 221 comprises a second primary subbranch 224a and a second tertiary subbranch 224c. As indicated, the ruptured subbranch of the second electrode 221 has not greatly compromised the functionality of the second electrode 221 as such, as there may still be a current conducted between the first primary subbranch 124a and the second primary subbranch 224a, between the first secondary subbranch 124b and the second tertiary subbranch 224c, and between the first tertiary subbranch 124c and the second tertiary subbranch 224c (and/or any other combination of subbranches connected to the first main branch 123 and subbranches connected to the second main branch 223). Thereby, the loss of a single subbranch has not compromised the functionality of the entire second electrode 221, but only the ability to conduct a current in the vicinity of the ruptured subbranch.

Figure 8:
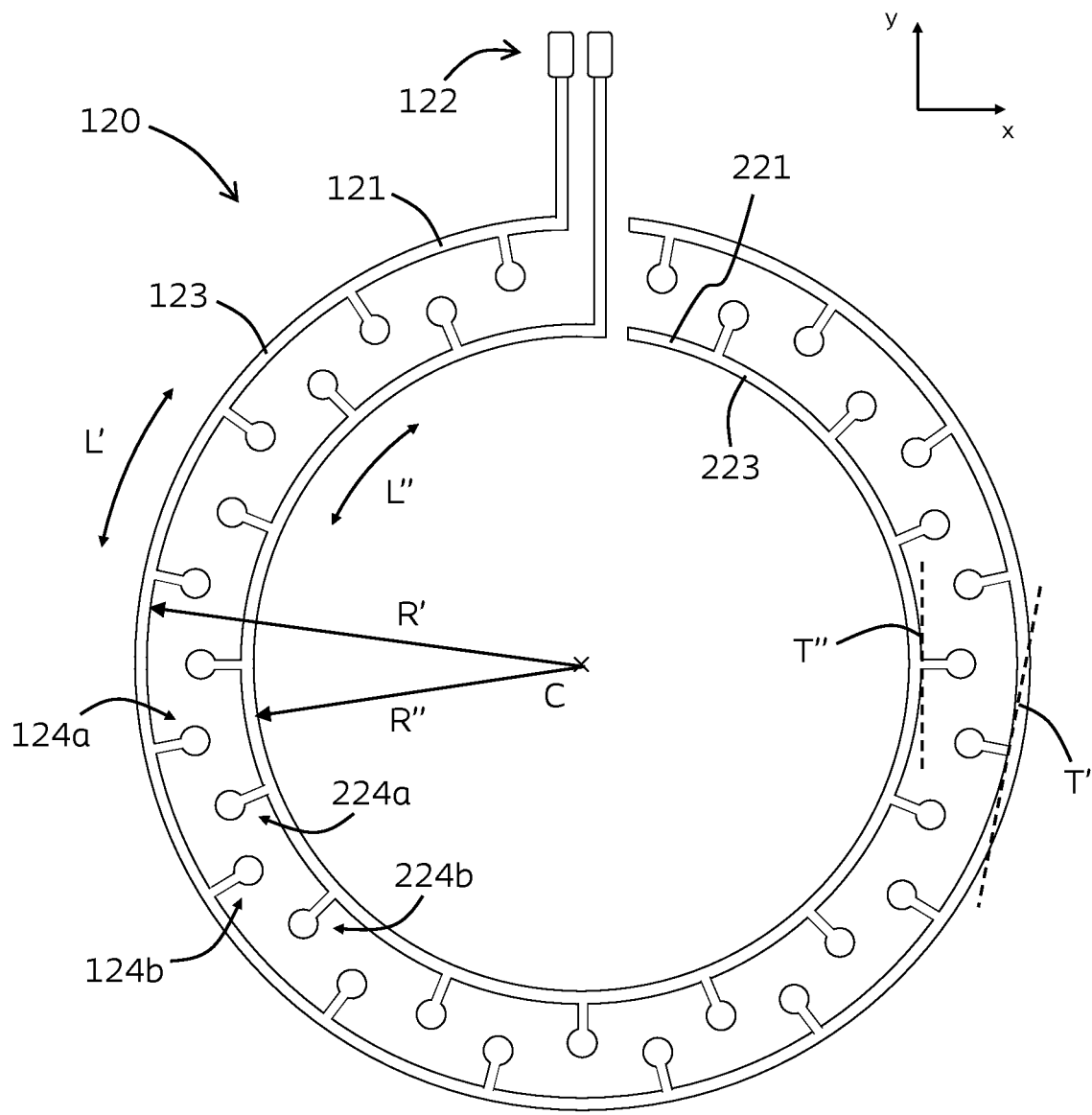
FIG. 8 illustrates an electrode assembly of a sensor assembly according to an embodiment of the invention.

FIG. 8 illustrates a top-view of an exemplary electrode assembly 120 comprising a first electrode 121 and a second electrode 221. The electrodes 121,221 terminate in terminals forming a monitor interface 122, such that a monitor device may be connected to the electrodes, such as to apply a voltage.

The first electrode 121 comprises a first main branch 123 extending along a first main path L' being circular about a centre point C. The first main branch 123 is arranged at a first radial distance R' from the centre point C. The second electrode 221 comprises a second main branch 223 extending along a first main path L" being circular about a centre point C. The second main branch 123 is arranged at a second radial distance R" from the centre point C. The first radial distance R' is greater than the second radial distance R', such that the first main branch 123 and the second main branch 223 are concentric about the centre point C.

A first tangent T' being a tangent to the first main path L' at a certain connection point between a subbranch of the first electrode 121 and the first main branch 123 and a second tangent T" being a tangent to the second main path L" at a certain connection between a subbranch of the second electrode 221 and the second main branch 223 have been included to aid a discussion of a first primary angle and second primary angle defining the angles by which the subbranches are arranged relative to the main branches.

The first electrode 121 comprises a first plurality of subbranches including a first primary subbranch 124a and a first secondary subbranch 124b. The second electrode 221 comprises a second plurality of subbranches including a second primary subbranch 224a and a second secondary subbranch 224b. According to the illustrated embodiment, the first main branch 123 and the second main branch 223 are parallel, i.e., the first main path L' and the second main path L" are parallel. According to the illustrated embodiment, the first plurality of subbranches including the first primary subbranch 124a and the first secondary subbranch 124b extend towards the second main branch 223, and the second plurality of subbranches including the second primary subbranch 224a and the second secondary subbranch 224b extend towards the first main branch 123. Thereby, a space between the first and second main branches is occupied by subbranches, such that sensing may occur in this space.

Figure 9:
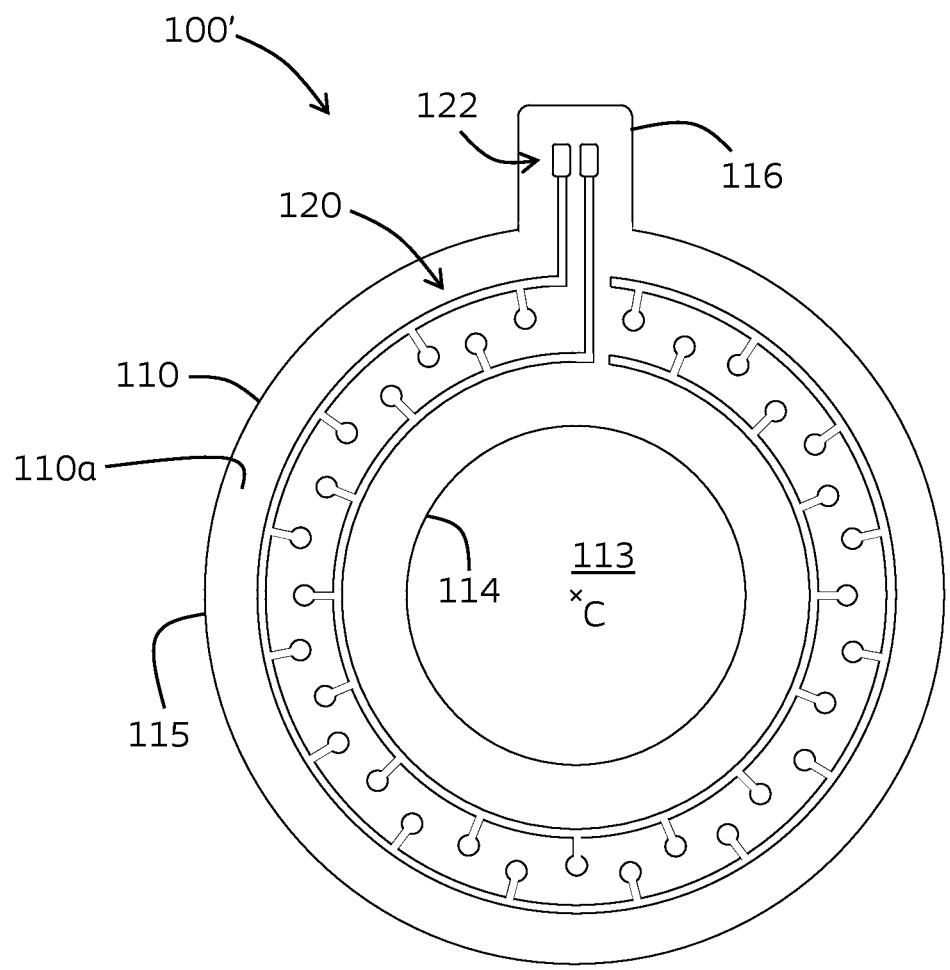
FIG. 9 illustrates a sensor assembly according to an embodiment of the invention.

FIG. 9 illustrates a sensor assembly 100' according to an embodiment of the invention, the sensor assembly 100' comprising the electrode assembly 120 of FIG. 8 arranged on a surface, such as on the proximal surface 110a, of a support layer 110. The support layer 110 has a stomal opening 113 with a centre point C. The stomal opening 113 may be defined by an inner periphery 114 of the support layer 110. Further, the support layer 110 may be delimited by an outer periphery 115, such that the electrode assembly 120 is arranged on the proximal surface 110a of the support layer 110 between the inner periphery 114 and the outer periphery 115. The support layer 110 extends into a neck portion 116 carrying the monitor interface 122, thereby reflecting the layout of the electrode assembly 120.

Figure 10A:
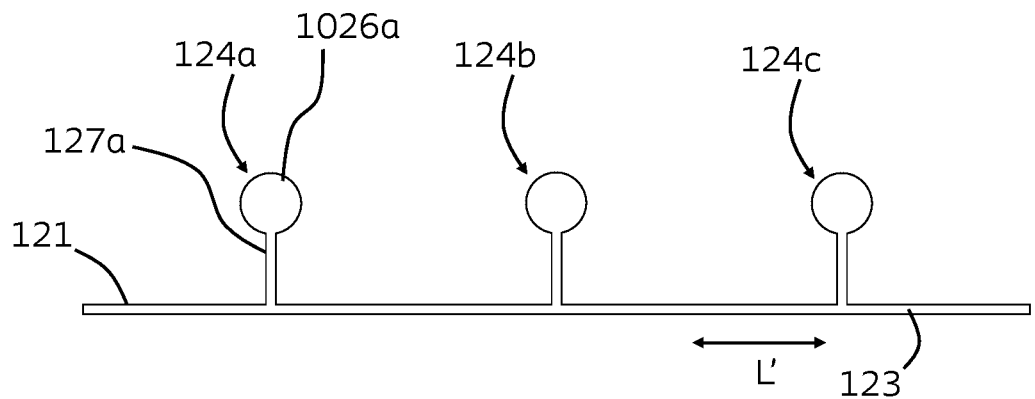
FIG. 10A illustrates a segment of a first electrode of a sensor assembly according to an embodiment of the invention.
Figure 10B:
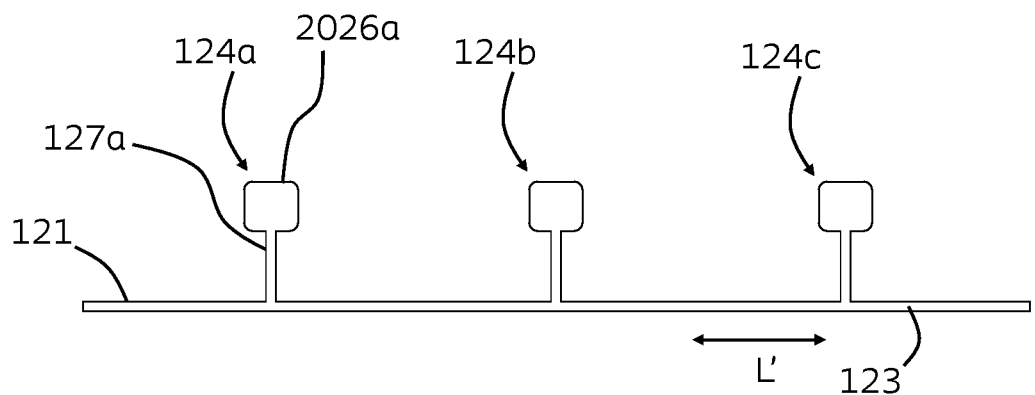
FIG. 10B illustrates a segment of a first electrode of a sensor assembly according to an embodiment of the invention.
Figure 10C:
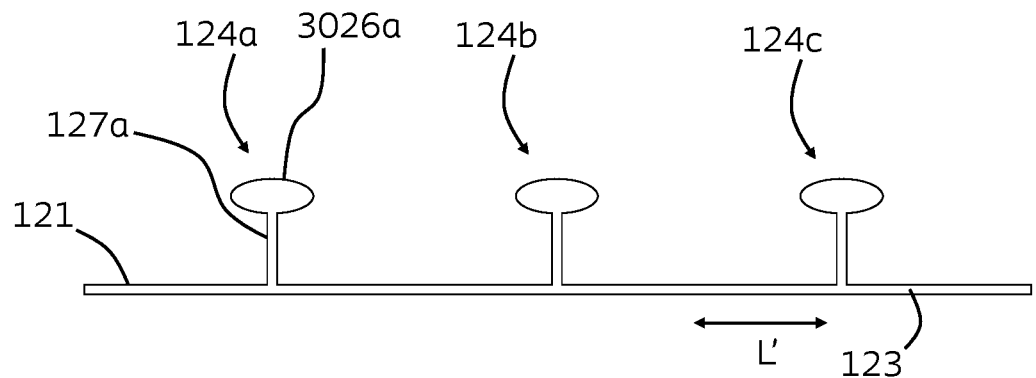
FIG. 10C illustrates a segment of a first electrode of a sensor assembly according to an embodiment of the invention.

FIGS. 10A-10C illustrate exemplary segments of a first electrode 121 comprising subbranches 124a,124b,124c having sensing parts 1026a,2026a,3026a of different exemplary shapes. In FIG. 10A, the sensing part 1026a is circular, in FIG. 10B, the sensing part 2026b is rectangular, and in FIG. 10C, the sensing part 3026a is oval. The shape of the sensing parts 1026a,2026a,3026a, along with the annular/ring-shaped sensing parts of previous embodiments, may be configured to correspond to a shape of openings in the masking layer as discussed previously. Further, the sensing part, irrespective of shape, may have a maximum diameter or diagonal being less than 5 mm, such as less than 3 mm, such as 2 mm or 1 mm.

Figure 11:
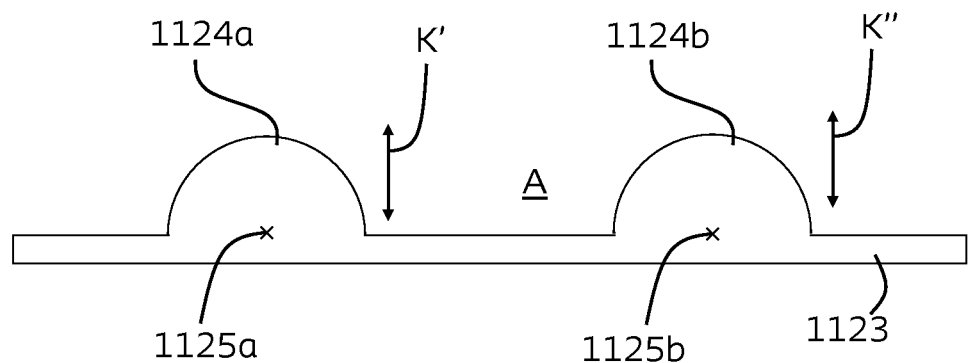
FIG. 11 illustrates a segment of a first electrode of a sensor assembly according to an embodiment of the invention.

FIG. 11 illustrates an exemplary segment of a first electrode 121 comprising subbranches 1124a,1124b in the shape of blots arranged on a first side A of, and integral with, the first main branch 1123, such as in the shape of semicircles. For example, where the first electrode 121 is a conductive trace, such as comprising conductive ink, the first primary subbranch 1124a may be a blot/semicircle of ink extending in a first primary direction K' relative to a tangent (not shown), here perpendicular, to the first main branch 1123 at respective first primary connection point 1125a (here, indicated as the centre of the respective semicircle), and the first secondary subbranch 1124b may be a semicircle of ink extending in a first secondary direction K" relative to a tangent (not shown), here perpendicular, to the first main branch 1123 at respective first secondary connection point 1125b (here, indicated as the centre of the respective semicircle).

Figure 12:
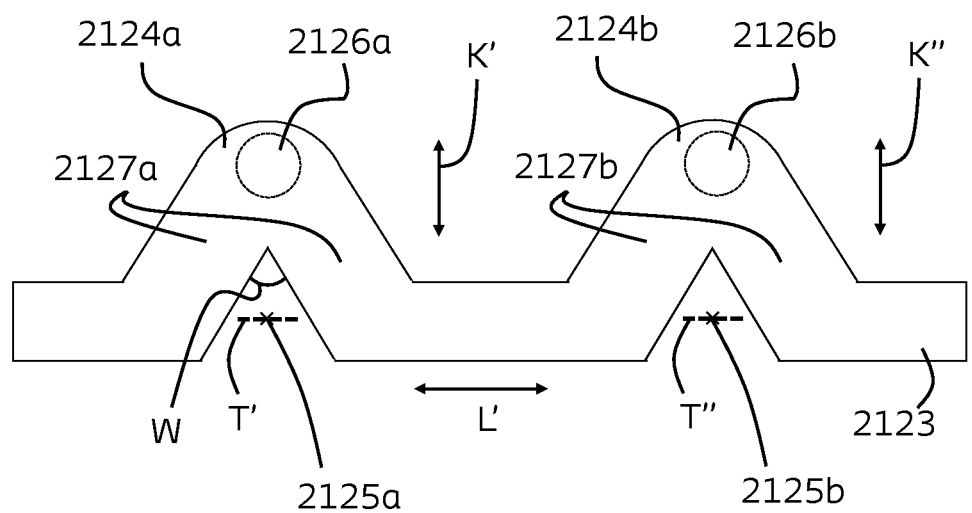
FIG. 12 illustrates a segment of a first electrode of a sensor assembly according to an embodiment of the invention.

FIG. 12 illustrates an exemplary segment of a first electrode 121 comprising subbranches 2124a,2124b defined by a displacement, or bend, of the first main branch 2123 in a first primary direction K' and a second primary direction K", respectively, at respective connection points 2125a,2125b, relative to the first main path L' of said first main branch 2123. In other words, each subbranch 2124a,2124b is in the shape of an elbow bend of the first main branch 2123, the elbow bend being in a first primary/secondary direction K',K" relative to a respective tangent T',T" of the first main path L'. Here, the tangents T',T" are parallel with the first main path L'. The connection points 2125a,2125b may be considered imaginary but indicate the position of the elbow bend along the first main path L' of the first main branch 2123. Preferably, the first primary/secondary directions K',K" are perpendicular (90 degrees) to the respective tangents T',T", such that the elbow bend is symmetric about a symmetry line parallel with the respective first primary/secondary direction K',K" at respective connection points 2125a,2125b. The indentation/acute angle W formed by the elbow bend may provide for a reduction of the amount of material used to form each subbranch and as such of the electrode as such. The size of the acute angle W of the elbow bend may be smaller or larger. For example, the size of the acute angle W may be maximally 90 degrees, such as maximally 45 degrees, such as maximally 30 degrees.

The subbranches 2124a,2124b may comprise solely curved corners/bends and/or edges, and as such, the illustrated embodiment should not be considered limiting to the scope.

The apexes, as indicated by a dotted circle, of each of the first primary subbranch 2124a and the first secondary subbranch 2124b may be considered respective first primary sensing part 2126a and first secondary sensing part 2126b, according to previous embodiments. The legs 2127a,2127b of the elbow bend may be considered the stem (e.g., a split/two-part stem) of the respective subbranch, according to previous embodiments.

Whereas mainly a first electrode and a second electrode have been discussed throughout the present disclosure and in the figures, it is to be understood that a plurality of electrodes, such as three or more electrodes, may carry the structural features of the first and second electrode as disclosed herein. Thus, the present disclosure intends to at least disclose structural features of an electrode, such as at least one electrode, but it is to be understood that a plurality of electrodes carrying such structural features may be included in the electrode assembly without departing from the scope of the invention.

Although particular features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications, and equivalents.

The invention claimed is:

1. A sensor assembly for an ostomy appliance, the sensor assembly comprising:
   a support layer, and
   a planar electrode assembly arranged on a surface of the support layer, the electrode assembly comprising at least a first electrode;
   wherein the first electrode comprises a first main branch extending along a first main path and a first plurality of subbranches connected to the first main branch, the first plurality of subbranches including a first primary subbranch and a first secondary subbranch, wherein the first primary subbranch is connected to the first main branch at a first primary connection point and extending in a first primary direction at a first primary angle relative to a tangent to the first main path at the first primary connection point, and
   wherein the first secondary subbranch is connected to the first main branch at a first secondary connection point and extending in a first secondary direction at a first secondary angle relative to a tangent to the first main path at the first secondary connection point, and
   wherein the first primary subbranch and the first secondary subbranch are symmetrical about a line of symmetry parallel with the first primary direction and the first secondary direction, respectively.

2. The sensor assembly according to claim 1, wherein the first primary angle and the first secondary angle are 90 degrees.

3. The sensor assembly according to claim 1, wherein the first primary subbranch comprises a first primary sensing part and a first primary stem connecting the first main branch and the first primary sensing part, and wherein the first secondary subbranch comprises a first secondary sensing part and a first secondary stem connecting the first main branch and the first secondary sensing part.

4. The sensor assembly according to claim 3, wherein the first main branch has a width being larger than a width of the first primary stem and a width of the first secondary stem.

5. The sensor assembly according to claim 1, wherein the first electrode is a conductive trace.

6. The sensor assembly according to claim 1, wherein the first main path is circular about a centre point configured to coincide with a centre point of a stomal opening of the ostomy appliance.

7. The sensor assembly according to claim 1, further comprising an insulative masking layer comprising a plurality of openings including a primary opening and a secondary opening, wherein the electrode assembly is arranged between the support layer and the masking layer.

8. The sensor assembly according to claim 7, wherein the first primary subbranch comprises a first primary sensing part and a first primary stem connecting the first main branch and the first primary sensing part, and wherein the first secondary subbranch comprises a first secondary sensing part and a first secondary stem connecting the first main branch and the first secondary sensing part, and wherein the primary opening coincides with the first primary sensing part and the secondary opening coincides with the first secondary sensing part.

9. The sensor assembly according to claim 1, further comprising an adhesive layer with a proximal side configured for attachment of the sensor assembly to the skin surface of a user, the adhesive layer having a stomal opening.

10. The sensor assembly according to claim 1, wherein the electrode assembly further comprises a second electrode, wherein the second electrode comprises a second main branch extending along a second main path and a second plurality of subbranches connected to the second main branch, the second plurality of subbranches including a second primary subbranch and a second secondary subbranch.

11. The sensor assembly according to claim 10, wherein the first main branch and the second main branch are substantially parallel.

12. The sensor assembly according to claim 10, wherein the first primary subbranch and the first secondary subbranch extend towards the second main branch of the second electrode, and wherein the second primary subbranch and the second secondary subbranch extend towards the first main branch of the first electrode.

13. A method of manufacturing a sensor assembly for an ostomy appliance, the method comprising:
   providing a support layer, and
   printing with a conductive ink, on a surface of the support layer, an electrode assembly comprising at least a first electrode comprising a first main branch extending along a first main path and a first plurality of subbranches connected to the first main branch, the first plurality of subbranches including a first primary subbranch and a first secondary subbranch,
   wherein the first primary subbranch is connected to the first main branch at a first primary connection point and extending in a first primary direction at a first primary angle relative to a tangent to the first main path at the first primary connection point, and
   wherein the first secondary subbranch is connected to the first main branch at a first secondary connection point and extending in a first secondary direction at a first secondary angle relative to a tangent to the first main path at the first secondary connection point, and
   wherein the first primary subbranch and the first secondary subbranch are symmetrical about a line of symmetry parallel with the first primary direction and the first secondary direction, respectively.

14. A base plate for an ostomy appliance, the base plate comprising:
   a first adhesive layer with a proximal side configured for attachment of the base plate to the skin surface of a user, the first adhesive layer having a stomal opening, and
   a sensor assembly, the sensor assembly comprising:
      a support layer, and
      a planar electrode assembly arranged on a surface of the support layer, the electrode assembly comprising at least a first electrode;
      wherein the first electrode comprises a first main branch extending along a first main path and a first plurality of subbranches connected to the first main branch, the first plurality of subbranches including a first primary subbranch and a first secondary subbranch, wherein the first primary subbranch is connected to the first main branch at a first primary connection point and extending in a first primary direction at a first primary angle relative to a tangent to the first main path at the first primary connection point, and wherein the first secondary subbranch is connected to the first main branch at a first secondary connection point and extending in a first secondary direction at a first secondary angle relative to a tangent to the first main path at the first secondary connection point, and wherein the first primary subbranch and the first secondary subbranch are symmetrical about a line of symmetry parallel with the first primary direction and the first secondary direction, respectively, and wherein the electrode assembly of the sensor assembly is arranged between a distal side of the first adhesive layer and the support layer of the sensor assembly.

15. A sensor patch for attachment to a base plate of an ostomy appliance, the sensor patch comprising:

a first adhesive layer with a proximal side configured for attachment of the sensor patch to the skin surface of a user, the first adhesive layer having a stomal opening, and a sensor assembly, the sensor assembly comprising:
a support layer, and
a planar electrode assembly arranged on a surface of the support layer, the electrode assembly comprising at least a first electrode;

wherein the first electrode comprises a first main branch extending along a first main path and a first plurality of subbranches connected to the first main branch, the first plurality of subbranches including a first primary subbranch and a first secondary subbranch, wherein the first primary subbranch is connected to the first main branch at a first primary connection point and extending in a first primary direction at a first primary angle relative to a tangent to the first main path at the first primary connection point, and wherein the first secondary subbranch is connected to the first main branch at a first secondary connection point and extending in a first secondary direction at a first secondary angle relative to a tangent to the first main path at the first secondary connection point, and wherein the first primary subbranch and the first secondary subbranch are symmetrical about a line of symmetry parallel with the first primary direction and the first secondary direction, respectively, and wherein the electrode assembly of the sensor assembly is arranged between a distal side of the first adhesive layer and the support layer of the sensor assembly.

* * * * *